United States Patent
Smits

(10) Patent No.: US 11,060,117 B2
(45) Date of Patent: Jul. 13, 2021

(54) PROCESS FOR ENZYMATIC HYDROLYSIS OF LIGNOCELLULOSIC MATERIAL AND FERMENTATION OF SUGARS

(71) Applicant: DSM IP ASSETS B.V., Heerlen (NL)

(72) Inventor: Johannes Petrus Smits, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/552,304

(22) Filed: Aug. 27, 2019

(65) Prior Publication Data

US 2019/0382806 A1 Dec. 19, 2019

Related U.S. Application Data

(63) Continuation of application No. 15/544,827, filed as application No. PCT/EP2016/051634 on Jan. 27, 2016, now Pat. No. 10,435,719.

(30) Foreign Application Priority Data

Jan. 28, 2015 (EP) ..................................... 15152901

(51) Int. Cl.
| | |
|---|---|
| *C12P 7/10* | (2006.01) |
| *C12P 7/04* | (2006.01) |
| *C12P 7/06* | (2006.01) |
| *C12N 1/14* | (2006.01) |
| *C12R 1/645* | (2006.01) |
| *C12P 7/00* | (2006.01) |

(52) U.S. Cl.
CPC ............... *C12P 7/10* (2013.01); *C12N 1/14* (2013.01); *C12P 7/04* (2013.01); *C12P 7/06* (2013.01); *C12R 1/645* (2013.01); *C12P 7/00* (2013.01); *Y02E 50/10* (2013.01); *Y02P 20/10* (2015.11)

(58) Field of Classification Search
None
See application file for complete search history.

(56) References Cited

U.S. PATENT DOCUMENTS

| | | | |
|---|---|---|---|
| 10,435,719 B2 * | 10/2019 | Smits | .................. C12N 1/14 |
| 2014/0170723 A1 | 6/2014 | Dobson et al. | |
| 2014/0356915 A1 | 12/2014 | Retsina | |
| 2018/0010154 A1 | 1/2018 | Smits | |

FOREIGN PATENT DOCUMENTS

| | | |
|---|---|---|
| CN | 102776244 A | 11/2012 |
| WO | 0132715 A1 | 5/2001 |
| WO | 2011137150 A1 | 11/2011 |
| WO | 2013106113 A2 | 7/2013 |
| WO | 2014144574 A1 | 9/2014 |

OTHER PUBLICATIONS

Hsieh, Chia-wen C., et al. "Cellulase inhibition by high concentrations of monosaccharides." Journal of agricultural and food chemistry, (2014), vol. 62, No. 17: 3800-3805.

Qing Qing, et al. "Xylooligomers are strong inhibitors of cellulose hydrolysis by enzymes." Bioresource technology , (2010), vol. 101, No. 24: 9624-9630.

Zehui, Jiang. "China Forestry Engineering," JiNan Press, May 2002.

\* cited by examiner

*Primary Examiner* — Anand U Desai
(74) *Attorney, Agent, or Firm* — McBee Moore & Vanik IP, LLC

(57) ABSTRACT

The invention relates to an integrated process for alcohol production from lignocellulosic material.

13 Claims, No Drawings

PROCESS FOR ENZYMATIC HYDROLYSIS OF LIGNOCELLULOSIC MATERIAL AND FERMENTATION OF SUGARS

CROSS REFERENCE TO RELATED APPLICATIONS

This application is a Continuation of U.S. application Ser. No. 15/544,827, filed 19 Jul. 2017, which is a National Stage entry of International Application No. PCT/EP2016/051634, filed 27 Jan. 2016, which claims priority to European Patent Application No. 15152901.3, filed 28 Jan. 2015. Each of these applications is incorporated by reference in its entirety.

BACKGROUND

Field of the Invention

The invention relates to an integrated process for alcohol production from lignocellulosic material.

Description of Related Art

Lignocellulosic material is primarily composed of cellulose, hemicellulose and lignin and provides an attractive platform for generating alternative energy and chemical sources to fossil fuels. The material is available in large amounts and can be converted into sugars which again can be converted into valuable fermentation products, such as biofuel and organic acids.

Producing fermentation products from lignocellulosic material is known in the art and generally includes the steps of pretreatment, hydrolysis, fermentation, and optionally recovery of the fermentation products.

During the hydrolysis, which may comprise the steps of liquefaction, pre-saccharification and/or saccharification, cellulose present in the lignocellulosic material is partly (typically 30 to 95%, dependable on enzyme activity and hydrolysis conditions) converted into reducing sugars by cellulolytic enzymes. The hydrolysis typically takes place during a process lasting 6 to 168 hours (see Kumar, S., Chem. Eng. Technol. 32 (2009), 517-526) under elevated temperatures of 45 to 70° C. and non-sterile conditions. Commonly, the sugars are then converted into valuable fermentation products, such as ethanol and succinic acid, by microorganisms, like yeast.

Succinic acid is a well-known four-carbon organic acid that has high value, since it can be used as a precursor for many important industrial chemicals and consumer products. Currently, succinic acid is produced petrochemically from butane through maleic anhydride. However, much attention has recently been focused on the microbiological production of succinic acid using microorganisms as an alternative to chemical synthesis.

In recent years, largely in response to uncertain fuel supply and efforts to reduce carbon dioxide emissions, production of ethanol from renewable biomass resources is becoming extremely important from the viewpoint of the global environment. Bioethanol is seen as a good fuel alternative, because the source crops can be grown renewably and in most climates around the world. In addition, the use of bioethanol is generally $CO_2$ neutral.

In recent years, the concept of the biorefinery has emerged. In the biorefinery concept biomass conversion processes and technology to produce a variety of products including fuels, power, chemicals and feed for cattle are integrated. This way advantage of the natural differences in the chemical and structural composition of the biomass feed stocks is taken. Careful management and utilization of materials, products and wastes are desirable, making the biorefinery concept a clear example of industrial symbiosis. By producing multiple products and integrating waste treatment, biorefineries can maximize the values derived from biomass feed stocks and turn biomass processing into real opportunities.

Optimization of processes performed within biorefineries and the overall design of biorefineries are crucial tools to increase efficiency of biorefineries and reduce their overall costs.

It is therefore desirable to include new and innovative concepts, designs and process configurations aimed at maximizing the output of biorefineries and reducing their overall costs.

SUMMARY

An object of the invention is to provide an improved integrated process for alcohol production from lignocellulosic material. Optimization and improvement lies in many features including, but not limited to, valorisation of side streams, separation of streams, (re-)use of certain materials and streams, conditions of enzymatic hydrolysis and fermentations, integration of a variety of conversion processes. Preferably, the integrated process for alcohol production from lignocellulosic material comprises the steps of:
  enzymatic hydrolysis of the lignocellulosic material to obtain enzymatically hydrolysed lignocellulosic material,
  solid/liquid separation of the enzymatically hydrolysed lignocellulosic material to obtain at least a solid fraction and at least a liquid fraction,
  fermentation of the at least solid fraction and/or the at least liquid fraction by an alcohol producing microorganism to produce alcohol,
  propagation of the alcohol producing microorganism by fermentation of the at least liquid fraction and/or the at least solid fraction,
  propagation of an enzyme producing microorganism, and
  production of enzymes by the enzyme producing microorganism.

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element. The term "microorganism" as used herein means one or more microorganisms. Unless stated differently, the terms "the at least a solid fraction" and "the at least a liquid fraction" mean the at least solid fraction and the at least liquid fraction, respectively, as obtained after solid/liquid separation of the enzymatically hydrolysed lignocellulosic material. As described herein after a solid/liquid separation at least a solid fraction and at least a liquid fraction are obtained. "The at least solid fraction" and "the at least liquid fraction" refer to the result of a separation step and can also be replaced by the terms "the solid fraction" and "the liquid fraction", respectively.

The invention relates to an integrated process of producing alcohol. The term "integrated process" is known to a person skilled in the art and means a process wherein two or more related process steps of at least two separate industrial processes, which can be separately performed, are combined, so that at least one process step is common for the two processes. Moreover, in an "integrated process" as defined herein streams, fractions and/or portions produced and/or obtained in one industrial process can be used in another industrial process thereby improving the overall process efficiently more than the sum of each individual process. The integrated process optimizes the utilization of biomass and reduces by-products that otherwise would require treatment. In other words, the term "integrated process" means a combination of at least two unit operations which exploits the interactions between different units in order to employ resources effectively, improve energy efficiency, improve material balance, maximize profit and/or minimize costs. At least one of the two unit operations receives material and/or energy, and may be dependent on these, from the other unit operation. In an integrated process the interactions between different unit operations are considered from the outset, rather than having them optimized separately. Process integration is not limited to the design of new plants, but it also covers retrofit design, for example new units to be installed in an old plant, and the operation of existing systems. The present invention also provide alcohol and organic acid production processes, wherein the units of such processes are completely integrated, and thus the processes are of low cost, simple operation and versatile due to the alternatives and interconnections within their steps. The integrated process is more energy and materials efficient than the individual processes together, and, as such, it yields a higher productivity with complete utilization and valorization of the lignocellulosic biomass.

The present invention relates to an integrated process for alcohol production from lignocellulosic material, wherein the process comprises:
  enzymatic hydrolysis of the lignocellulosic material to obtain enzymatically hydrolysed lignocellulosic material,
  solid/liquid separation of the enzymatically hydrolysed lignocellulosic material to obtain at least a solid fraction and at least a liquid fraction,
  fermentation of the at least solid fraction and/or the at least liquid fraction by an alcohol producing microorganism to produce alcohol,
  propagation of the alcohol producing microorganism by fermentation of the at least liquid fraction and/or the at least solid fraction,
  propagation of an enzyme producing microorganism, and
  production of enzymes by the enzyme producing microorganism.

The present invention also relates to an integrated process for alcohol production from lignocellulosic material, wherein the process comprises:
  pretreatment of the lignocellulosic material to obtain pretreated lignocellulosic material,
  enzymatic hydrolysis of the pretreated lignocellulosic material to obtain enzymatically hydrolysed lignocellulosic material,
  solid/liquid separation of the enzymatically hydrolysed lignocellulosic material to obtain at least a solid fraction and at least a liquid fraction,
  fermentation of the at least solid fraction and/or the at least liquid fraction by an alcohol producing microorganism to produce alcohol,
  propagation of the alcohol producing microorganism by fermentation of the at least liquid fraction and/or the at least solid fraction,
  propagation of an enzyme producing microorganism, and
  production of enzymes by the enzyme producing microorganism.

In an embodiment the integrated processes for alcohol production according to the present invention may also comprise the steps of fermentation of the at least liquid fraction and/or the at least solid fraction by an organic acid producing microorganism to produce an organic acid and/or propagation of the organic acid producing microorganism by fermentation of the at least liquid fraction and/or the at least solid fraction. In that case the integrated process of the invention can be seen as an integrated process for alcohol production and organic acid production. In an embodiment the at least liquid fraction is used as substrate in the production of an organic acid by the organic acid producing microorganism. In other words, the organic acid producing microorganism ferments the at least liquid fraction to produce an organic acid. In an embodiment the organic acid producing microorganism does not ferment the at least solid fraction to produce an organic acid. In an embodiment the alcohol produced by the alcohol producing microorganism is used as a substrate in the fermentation by the organic acid producing microorganism.

In an embodiment the at least liquid fraction is used as substrate in the production of alcohol by the alcohol producing microorganism. In other words, the alcohol producing microorganism ferments the at least liquid fraction to produce alcohol. In an embodiment the alcohol producing microorganism does not ferment the at least solid fraction to produce alcohol. In an embodiment the liquid fraction obtained after solid/liquid separation of the lignocellulosic material and/or the pretreated lignocellulosic material is used as substrate in the production of alcohol by the alcohol producing microorganism. In an embodiment the at least liquid fraction and the liquid fraction obtained after solid/liquid separation of the lignocellulosic material and/or the pretreated lignocellulosic material is used as substrate in the production of alcohol by the alcohol producing microorganism. In an embodiment the enzymatically hydrolysed lignocellulosic material is used as substrate in the production of alcohol by the alcohol producing microorganism. In other words, the enzymatically hydrolysed lignocellulosic material, before it is subjected to a solid/liquid separation, is used as substrate in the production of alcohol by the alcohol producing microorganism.

In an embodiment the present invention relates to an integrated process for alcohol production from lignocellulosic material as described herein, wherein the process comprises the step of propagation of the alcohol producing microorganism by fermentation of the at least liquid fraction and/or the at least solid fraction. If necessary, one or more external carbon and nutrient sources can be added before and/or during the propagation. Conditions for propagation will depend on the type of microorganism used and are well within the scope of the skilled artisan.

In an embodiment the present invention relates to an integrated process for alcohol production from lignocellulosic material as described herein, wherein the process also comprises the step of propagation of the organic acid producing microorganism by fermentation of the at least liquid fraction and/or the at least solid fraction. If necessary, one or more external carbon and nutrient sources can be added before and/or during the propagation. Conditions for propagation will depend on the type of microorganism used and are well within the scope of the skilled artisan.

In an embodiment the present invention relates to an integrated process for alcohol production from lignocellulosic material as described herein, wherein the process comprises the step of propagation of an enzyme producing microorganism. If necessary, one or more external carbon and nutrient sources can be added before and/or during the propagation. Conditions for propagation will depend on the type of microorganism used and are well within the scope of the skilled artisan.

In an embodiment the present invention relates to an integrated process for alcohol production from lignocellulosic material as described herein, wherein the process comprises the step of production of enzymes by an enzyme producing microorganism. If necessary, one or more external carbon and nutrient sources can be added before and/or during the production. Conditions for production will depend on the type of microorganism used and are well within the scope of the skilled artisan.

In an embodiment the present invention relates to an integrated process for alcohol production from lignocellulosic material, wherein the process comprises:
  enzymatic hydrolysis of the lignocellulosic material to obtain enzymatically hydrolysed lignocellulosic material,
  solid/liquid separation of the enzymatically hydrolysed lignocellulosic material to obtain at least a solid fraction and at least a liquid fraction,
  fermentation of the at least solid fraction and/or the at least liquid fraction by an alcohol producing microorganism to produce alcohol,
  fermentation of the at least liquid fraction and/or the at least solid fraction by an organic acid producing microorganism to produce an organic acid,
  propagation of the alcohol producing microorganism by fermentation of the at least liquid fraction and/or the at least solid fraction,
  propagation of the organic acid producing microorganism by fermentation of the at least liquid fraction and/or the at least solid fraction,
  propagation of an enzyme producing microorganism, and
  production of enzymes by the enzyme producing microorganism.

In an embodiment the present invention relates to an integrated process for alcohol production from lignocellulosic material, wherein the process comprises:
  pretreatment of the lignocellulosic material to obtain pretreated lignocellulosic material,
  enzymatic hydrolysis of the pretreated lignocellulosic material to obtain enzymatically hydrolysed lignocellulosic material,
  solid/liquid separation of the enzymatically hydrolysed lignocellulosic material to obtain at least a solid fraction and at least a liquid fraction,
  fermentation of the at least solid fraction and/or the at least liquid fraction by an alcohol producing microorganism to produce alcohol,
  fermentation of the at least liquid fraction and/or the at least solid fraction by an organic acid producing microorganism to produce an organic acid,
  propagation of the alcohol producing microorganism by fermentation of the at least liquid fraction and/or the at least solid fraction,
  propagation of the organic acid producing microorganism by fermentation of the at least liquid fraction and/or the at least solid fraction,
  propagation of an enzyme producing microorganism, and
  production of enzymes by the enzyme producing microorganism.

In an embodiment enzymatic hydrolysis and fermentation may be separate steps, but may also be combined. Examples include, but are not limited to, separate hydrolysis and fermentation (SHF), simultaneous saccharification and fermentation (SSF), simultaneous saccharification and co-fermentation (SSCF), hybrid hydrolysis and fermentation (HHF), separate hydrolysis and co-fermentation (SHCF), hybrid hydrolysis and co-fermentation (HHCF), and direct microbial conversion (DMC), also sometimes called consolidated bioprocessing (CBP).

In an embodiment the lignocellulosic material is subjected to at least one solid/liquid separation before the enzymatic hydrolysis. In an embodiment the pretreated lignocellulosic material is subjected to at least one solid/liquid separation before the enzymatic hydrolysis. So, before subjecting the lignocellulosic material and/or pretreated lignocellulosic material to enzymatic hydrolysis, it can be subjected to at least one solid/liquid separation. The methods and conditions of solid/liquid separation will depend on the type of lignocellulosic material used and are well within the scope of the skilled artisan. Examples include, but are not limited to, centrifugation, cyclonic separation, filtration, decantation, sieving and sedimentation. During solid/liquid separation, means and/or aids for improving the separation may be used.

In an embodiment the liquid fraction obtained after solid/liquid separation of the lignocellulosic material and/or the pretreated lignocellulosic material is subjected to enzymatic hydrolysis. The solid fraction obtained after solid/liquid separation of the lignocellulosic material and/or the pretreated lignocellulosic material is subjected to a further solid/liquid separation. This cycle can be repeated several times.

In another embodiment the solid fraction obtained after solid/liquid separation of the lignocellulosic material and/or the pretreated lignocellulosic material is subjected to enzymatic hydrolysis, while the liquid fraction obtained after solid/liquid separation of the lignocellulosic material and/or the pretreated lignocellulosic material is used as substrate in at least one of the fermentation processes. In an embodiment the liquid fraction obtained after solid/liquid separation of the lignocellulosic material and/or the pretreated lignocellulosic material is used as substrate in the propagation of the alcohol producing microorganism and/or is used as substrate in the fermentation by the alcohol producing microorganism to produce alcohol.

Before subjecting the lignocellulosic material and/or the pretreated lignocellulosic material to a solid/liquid separation step additional compounds such as a centrifugation aid can be added.

In an embodiment the enzymes used in the enzymatic hydrolysis can be added before subjecting the lignocellulosic material and/or the pretreated lignocellulosic material to a solid/liquid separation step. The enzymes then partly end up in the liquid fraction.

In an embodiment a part of the enzymatically hydrolysed lignocellulosic material is used in the propagation of the enzyme producing microorganism and/or the production of enzymes by the enzyme producing microorganism. In an embodiment the part of the enzymatically hydrolysed lignocellulosic material that is used in the propagation of the enzyme producing microorganism and/or the production of enzymes by the enzyme producing microorganism is the at least liquid fraction obtained after solid/liquid separation of the enzymatically hydrolysed lignocellulosic material. In an embodiment a part of the enzymatically hydrolysed lignocellulosic material and a part of the lignocellulosic material and/or the pretreated lignocellulosic material is used in the propagation of the enzyme producing microorganism and/or the production of enzymes by the enzyme producing microorganism. This means that a part of the enzymatically hydrolysed lignocellulosic material and/or a part of the lignocellulosic material and/or the pretreated lignocellulosic material is added to the enzyme producing microorganism before and/or during propagation and/or before and/or during production of enzymes by the enzyme producing microorganism. Of course, the enzyme producing microorganism can also be added to the part of the enzymatically hydrolysed lignocellulosic material and/or the part of the lignocellulosic material and/or the pretreated lignocellulosic material. The lignocellulosic material and/or the pretreated lignocellulosic material used in the propagation of the enzyme producing microorganism and/or the production of enzymes by the enzyme producing microorganism has not undergone enzymatic hydrolysis. In an embodiment the part of the lignocellulosic material and/or the pretreated lignocellulosic material that is used in the propagation of the enzyme producing microorganism and/or the production of enzymes by the enzyme producing microorganism has not been subjected to a solid/liquid separation. In another embodiment the part of the lignocellulosic material and/or the pretreated lignocellulosic material that is used in the propagation of the enzyme producing microorganism and/or the production of enzymes by the enzyme producing microorganism has been subjected to a solid/liquid separation. In the latter case, the solid fraction obtained after solid/liquid separation of the lignocellulosic material and/or the pretreated lignocellulosic material is used in the propagation of the enzyme producing microorganism and/or the production of enzymes by the enzyme producing microorganism.

In a preferred embodiment the enzymes produced by the enzyme producing microorganism are used in the enzymatic hydrolysis of the lignocellulosic material and/or the pretreated lignocellulosic material to obtain enzymatically hydrolysed lignocellulosic material.

In an embodiment the propagation of the enzyme producing microorganism and the production of enzymes by the enzyme producing microorganism are a single step, meaning that during propagation of the enzyme producing microorganism enzymes are already produced by the microorganism.

The enzymatically hydrolysed lignocellulosic material that is added to the enzyme producing microorganism before and/or during propagation of the enzyme producing microorganism and/or before and/or during production of enzymes by the enzyme producing microorganism can be concentrated before addition. In an embodiment the part of the enzymatically hydrolysed lignocellulosic material that is used in the propagation of the enzyme producing microorganism and/or the production of enzymes by the enzyme producing microorganism has been subjected to a solid/liquid separation. The liquid fraction obtained after solid/liquid separation of the enzymatically hydrolysed lignocellulosic material may be used in the propagation of the enzyme producing microorganism and/or the production of enzymes by the enzyme producing microorganism. In an embodiment that liquid fraction may be subjected to a concentration step before it is used in the propagation of the enzyme producing microorganism and/or the production of enzymes by the enzyme producing microorganism.

The lignocellulosic material and/or the pretreated lignocellulosic material that is added to the enzyme producing microorganism before and/or during propagation of the enzyme producing microorganism and/or before and/or during production of enzymes by the enzyme producing microorganism can be washed before addition.

In an embodiment the ratio between the part of the enzymatically hydrolysed lignocellulosic material and the part of the lignocellulosic material and/or the pretreated lignocellulosic material that are used in the propagation of the enzyme producing microorganism and/or the production of enzymes by the enzyme producing microorganism is between 1% wt: 99% wt and 99% wt: 1% wt. Of course, the ratio may differ in case one or more external carbon sources are used in the propagation of the enzyme producing microorganism and/or the production of enzymes by the enzyme producing microorganism. In an alternative embodiment, when the enzymatic hydrolysis comprises a separate liquefaction step and saccharification step (as described in more detail below), the product of the liquefaction step can be used in the propagation of the enzyme producing microorganism and/or the production of enzymes by the enzyme producing microorganism. This can be done with or without addition of enzymatically hydrolysed lignocellulosic material. Of course, also each and every combination of part of the enzymatically hydrolysed lignocellulosic material, part of the pretreated lignocellulosic material, product of the liquefaction step and external carbon and nutrient source can be used in the propagation of the enzyme producing microorganism and/or the production of enzymes by the enzyme producing microorganism.

The part of the enzymatically hydrolysed lignocellulosic material and the part of the lignocellulosic material and/or the pretreated lignocellulosic material that are used in the propagation of the enzyme producing microorganism and/or the production of enzymes by the enzyme producing microorganism can vary. The part of the enzymatically hydrolysed lignocellulosic material that is used in the propagation of the enzyme producing microorganism and/or the production of enzymes by the enzyme producing microorganism can be at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, at least 15 wt %, at least 20 wt % of the total enzymatically hydrolysed lignocellulosic material.

The part of the lignocellulosic material and/or the pretreated lignocellulosic material that is used in the propagation of the enzyme producing microorganism and/or the production of enzymes by the enzyme producing microorganism can be at least 1 wt %, at least 2 wt %, at least 3 wt %, at least 4 wt %, at least 5 wt %, at least 6 wt %, at least 7 wt %, at least 8 wt %, at least 9 wt %, at least 10 wt % of the total lignocellulosic material and/or the total pretreated lignocellulosic material.

Next to the enzymatically hydrolysed lignocellulosic material and the lignocellulosic material and/or the pretreated lignocellulosic material, at least one external carbon and nutrient source can be used in the propagation of the enzyme producing microorganism and/or the production of enzymes by the enzyme producing microorganism. The external carbon and nutrient source can have the function of inducer and/or nutrient. Of course, several different external carbon and nutrient sources may be added. Carbon and nutrient sources suitable in the propagation of an enzyme producing microorganism and/or in the production of enzymes by an enzyme producing microorganism are known to a person skilled in the art.

After enzymatic hydrolysis, the enzymatically hydrolysed lignocellulosic material is subjected to a solid/liquid separation. Methods for solid/liquid separation include, but are not limited to, centrifugation, cyclonic separation, filtration, decantation, sieving and sedimentation. During solid/liquid separation, means and/or aids may be used to improve the separation.

The solid/liquid separation leads to at least a solid fraction and at least a liquid fraction. In an embodiment the at least solid fraction comprises between 3 and 97 wt % C5 sugars. In an embodiment the at least liquid fraction comprises between 1 and 97 wt % C6 sugars.

In an embodiment the enzymatic hydrolysis comprises at least a liquefaction step wherein the lignocellulosic material and/or the pretreated lignocellulosic material is hydrolysed in at least a first container, and a saccharification step wherein the liquefied material is hydrolysed in the at least first container and/or in at least a second container. Saccharification can be done in the same container as the liquefaction (i.e. the at least first container), it can also be done in a separate container (i.e. at least a second container). So, in the enzymatic hydrolysis of the integrated processes according to the present invention liquefaction and saccharification may be combined. Alternatively, the liquefaction and saccharification may be separate steps. Liquefaction and saccharification may be performed at different temperatures, but may also be performed at a single temperature. In an embodiment the temperature of the liquefaction is higher than the temperature of the saccharification. Liquefaction is preferably carried out at a temperature of 60-75° C. and saccharification is preferably carried out at a temperature of 50-65° C.

The enzymatic hydrolysis can be performed in one or more containers, but can also be performed in one or more tubes or any other continuous system. This also holds true when the enzymatic hydrolysis comprises a liquefaction step and a saccharification step. The liquefaction step can be performed in one or more containers, but can also be performed in one or more tubes or any other continuous system and/or the saccharification step can be performed in one or more containers, but can also be performed in one or more tubes or any other continuous system. Examples of containers to be used in the present invention include, but are not limited to, fed-batch stirred containers, batch stirred containers, continuous flow stirred containers with ultrafiltration, and continuous plug-flow column reactors. Stirring can be done by one or more impellers, pumps and/or static mixers.

In an embodiment the lignocellulosic material and/or the pretreated lignocellulosic material can be added to the one or more containers used for the enzymatic hydrolysis. In an embodiment the enzymes used in the enzymatic hydrolysis are already present in the one or more containers before the lignocellulosic material and/or the pretreated lignocellulosic material is added. In another embodiment the enzymes used in the enzymatic hydrolysis can be added to the one or more containers. In an embodiment the lignocellulosic material and/or the pretreated lignocellulosic material is already present in the one or more containers before the enzymes used in the enzymatic hydrolysis are added. In an embodiment both the lignocellulosic material and/or the pretreated lignocellulosic material and the enzymes used in the enzymatic hydrolysis are added simultaneously to the one or more containers. The enzymes used in the enzymatic hydrolysis may be an aqueous composition. This paragraph also holds true when the enzymatic hydrolysis comprises a liquefaction step and a saccharification step.

The enzymes used in the enzymatic hydrolysis may be added before and/or during the enzymatic hydrolysis. As indicated above, when the lignocellulosic material and/or the pretreated lignocellulosic material is subjected to a solid/liquid separation before enzymatic hydrolysis, the enzymes used in the enzymatic hydrolysis may be added before the solid/liquid separation. Alternatively, they may also be added after solid/liquid separation or before and after solid/liquid separation. The enzymes may also be added during the enzymatic hydrolysis. In case the enzymatic hydrolysis comprises a liquefaction step and saccharification step, additional enzymes may be added during and/or after the liquefaction step. The additional enzymes may be added before and/or during the saccharification step. Additional enzymes may also be added after the saccharification step.

In an embodiment the total enzymatic hydrolysis time is 10 hours or more, 12 hours or more, 14 hours or more, 16 hours or more, 18 hours or more, 20 hours or more, 30 hours or more, 40 hours or more, 50 hours or more, 60 hours or more, 70 hours or more, 80 hours or more, 90 hours or more, 100 hours or more, 110 hours or more, 120 hours or more, 130 hours or more, 140 hours or more, 150 hours or more, 160 hours or more, 170 hours or more, 180 hours or more, 190 hours or more, 200 hours or more.

In an embodiment, the total enzymatic hydrolysis time is 10 to 300 hours, 16 to 275 hours, preferably 20 to 250 hours, more preferably 30 to 200 hours, most preferably 40 to 150 hours.

The viscosity of the lignocellulosic material in the one or more containers used for the enzymatic hydrolysis is kept between 10 and 4000 cP, between 10 and 2000 cP, preferably between 10 and 1000 cP.

In case the integrated process comprises an enzymatic hydrolysis comprising a liquefaction step and a saccharification step, the viscosity of the lignocellulosic material in the liquefaction step is kept between 10 and 4000 cP, between 10 and 2000 cP, preferably between 10 and 1000 cP and/or the viscosity of the lignocellulosic material in the saccharification step is kept between 10 and 1000 cP, between 10 and 900 cP, preferably between 10 and 800 cP.

The viscosity can be determined with a Brookfield DV III Rheometer at the temperature used for the hydrolysis.

In an embodiment oxygen is added during the enzymatic hydrolysis. In an embodiment oxygen is added during at least a part of the enzymatic hydrolysis. Oxygen can be added continuously or discontinuously during the enzymatic hydrolysis. In an embodiment oxygen is added one or more times during the enzymatic hydrolysis. In an embodiment oxygen may be added before the enzymatic hydrolysis, during the addition of lignocellulosic material to a container used of enzymatic hydrolysis, during the addition of enzyme to a container used of enzymatic hydrolysis, during a part of the enzymatic hydrolysis, during the whole enzymatic hydrolysis or any combination thereof. Oxygen is added to the one or more containers used in the enzymatic hydrolysis.

Oxygen can be added in several forms. For example, oxygen can be added as oxygen gas, oxygen-enriched gas, such as oxygen-enriched air, or air. Oxygen may also be added by means of in situ oxygen generation. For example, oxygen may be generated by electrolysis, oxygen may be produced enzymatically, e.g. by the addition of peroxide, or oxygen may be produced chemically, e.g. by an oxygen generating system such as $KHSO_5$. For example, oxygen is produced from peroxide by catalase. The peroxide can be added in the form of dissolved peroxide or generated by an enzymatic or chemical reaction. In case catalase is used as enzyme to produce oxygen, catalase present in the enzyme composition for the hydrolysis can be used or catalase can be added for this purpose.

Examples how to add oxygen include, but are not limited to, addition of oxygen by means of sparging, electrolysis, chemical addition of oxygen, filling the one or more containers used in the enzymatic hydrolysis from the top (plunging the hydrolysate into the tank and consequently introducing oxygen into the hydrolysate) and addition of oxygen to the headspace of said one or more containers. When oxygen is added to the headspace of the container(s), sufficient oxygen necessary for the hydrolysis reaction may be supplied. In general, the amount of oxygen added to the container(s) can be controlled and/or varied. Restriction of the oxygen supplied is possible by adding only oxygen during part of the hydrolysis time in said container(s). Another option is adding oxygen at a low concentration, for example by using an mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another way to control the oxygen concentration is to add an oxygen consumer and/or an oxygen generator. Oxygen can be introduced, for example blown, into the liquid hydrolysis container contents of lignocellulosic material. It can also be blown into the headspace of the container.

In an embodiment oxygen is added to the one or more containers used in the enzymatic hydrolysis before and/or during and/or after the addition of the lignocellulosic material and/or the pretreated lignocellulosic material to said one or more containers. The oxygen may be introduced together with the lignocellulosic material and/or the pretreated lignocellulosic material that enters the hydrolysis container(s). The oxygen may be introduced into the material stream that will enter the container(s) or with part of the container(s) contents that passes an external loop of the container(s).

In the enzymatic hydrolysis amorphous and crystalline polysaccharides or cellulose are hydrolysed to sugars such as glucose. Amorphous polysaccharides are for example converted to oligosaccharides by endoglucanases and then the oligosaccharides can be converted by cellobiohydrolases and beta-glucosidases to glucose. The conversion of the crystalline polysaccharides may occur in parallel or sequential and continue even when most of the amorphous polysaccharides are hydrolysed. The addition of oxygen in combination with lytic polysaccharide monooxygenases is beneficial during the hydrolysis of the crystalline polysaccharides for example in the degradation of the polysaccharides into oligosaccharides. The crystalline glucan structure can be opened by lytic polysaccharide monooxygenases. This type of enzyme opens up the structure by oxidizing the glycosidic bonds and making it accessible for the other cellulolytic enzymes for further hydrolysing the oligosaccharides into glucose. The addition of oxygen is very useful, especially in the phase wherein crystalline polysaccharides are converted by enzymes.

In an embodiment the container(s) used in the enzymatic hydrolysis of the integrated processes of the present invention have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$. In general, the container(s) will be smaller than 3000 $m^3$ or 5000 $m^3$. In case several containers are used in the enzymatic hydrolysis of the integrated processes of the present invention, they may have the same volume, but also may have a different volume. In case the enzymatic hydrolysis of the integrated processes of the present invention comprises a separate liquefaction step and saccharification step the container(s) used for the liquefaction step and the container(s) used for the saccharification step may have the same volume, but also may have a different volume.

In an embodiment the container(s) used in the fermentation of the at least solid fraction and/or the at least liquid fraction by an alcohol producing microorganism to produce alcohol have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$, at least 2000 $m^3$, at least 2500 $m^3$, at least 3000 $m^3$, at least 3500 $m^3$, at least 4000 $m^3$, at least 4500 $m^3$. In general, the container(s) will be smaller than 5000 $m^3$.

In an embodiment the container(s) used in the fermentation of the at least liquid fraction and/or the at least solid fraction by an organic acid producing microorganism to produce an organic acid have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$, at least 500 $m^3$, at least 600 $m^3$, at least 700 $m^3$, at least 800 $m^3$, at least 900 $m^3$, at least 1000 $m^3$, at least 1500 $m^3$. In general, the container(s) will be smaller than 2000 $m^3$.

In an embodiment the container(s) used in the propagation of the alcohol producing microorganism by fermentation of the at least liquid fraction and/or the at least solid fraction have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 $m^3$, at least 40 $m^3$, at least 45 $m^3$, at least 50 $m^3$, at least 60 $m^3$, at least 70 $m^3$, at least 75 $m^3$, at least 80 $m^3$, at least 90 $m^3$, at least 100 $m^3$, at least 200 $m^3$, at least 300 $m^3$, at least 400 $m^3$. In general, the container(s) will be smaller than 500 $m^3$.

In an embodiment the container(s) used in the propagation of the organic acid producing microorganism by fermentation of the at least liquid fraction and/or the at least solid fraction have a volume of at least 1 $m^3$. Preferably, the containers have a volume of at least 1 $m^3$, at least 2 $m^3$, at least 3 $m^3$, at least 4 $m^3$, at least 5 $m^3$, at least 6 $m^3$, at least 7 $m^3$, at least 8 $m^3$, at least 9 $m^3$, at least 10 $m^3$, at least 15 $m^3$, at least 20 $m^3$, at least 25 $m^3$, at least 30 $m^3$, at least 35 m³, at least 40 m³, at least 45 m³, at least 50 m³, at least 60 m³, at least 70 m³, at least 75 m³, at least 80 m³, at least 90 m³, at least 100 m³, at least 150 m³. In general, the container(s) will be smaller than 200 m³.

In an embodiment the container(s) used in the propagation of an enzyme producing microorganism have a volume of at least 1 m³. Preferably, the containers have a volume of at least 1 m³, at least 2 m³, at least 3 m³, at least 4 m³, at least 5 m³, at least 6 m³, at least 7 m³, at least 8 m³, at least 9 m³, at least 10 m³, at least 15 m³, at least 20 m³, at least 25 m³, at least 30 m³, at least 35 m³, at least 40 m³, at least 45 m³, at least 50 m³, at least 60 m³, at least 70 m³, at least 75 m³, at least 80 m³, at least 90 m³, at least 100 m³, at least 200 m³, at least 300 m³, at least 400 m³. In general, the container(s) will be smaller than 500 m³.

In an embodiment the container(s) used in the production of enzymes by the enzyme producing microorganism have a volume of at least 1 m³. Preferably, the containers have a volume of at least 1 m³, at least 2 m³, at least 3 m³, at least 4 m³, at least 5 m³, at least 6 m³, at least 7 m³, at least 8 m³, at least 9 m³, at least 10 m³, at least 15 m³, at least 20 m³, at least 25 m³, at least 30 m³, at least 35 m³, at least 40 m³, at least 45 m³, at least 50 m³, at least 60 m³, at least 70 m³, at least 75 m³, at least 80 m³, at least 90 m³. In general, the container(s) will be smaller than 100 m³.

In an embodiment the enzyme producing microorganism is a fungus. In an embodiment the enzymes are derived from a filamentous fungus or the enzymes comprise a filamentous fungal enzyme. In a preferred embodiment the fungus is *Rasamsonia*, with *Rasamsonia emersonii* being most preferred. The enzymes used in the enzymatic hydrolysis of the integrated processes of the present invention are derived from a fungus or the enzymes used in the enzymatic hydrolysis of the integrated processes of the present invention comprise a fungal enzyme. "Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Agaricus, Aspergillus, Aureobasidium, Beauvaria, Cephalosporium, Ceriporiopsis, Chaetomium paecilomyces, Chrysosporium, Claviceps, Cochiobolus, Coprinus, Cryptococcus, Cyathus, Emericella, Endothia, Endothia mucor, Filibasidium, Fusarium, Geosmithia, Gilocladium, Humicola, Magnaporthe, Mucor, Myceliophthora, Myrothecium, Neocallimastix, Neurospora, Paecilomyces, Penicillium, Piromyces, Panerochaete, Pleurotus, Podospora, Pyricularia, Rasamsonia, Rhizomucor, Rhizopus, Scylatidium, Schizophyllum, Stagonospora, Talaromyces, Thermoascus, Thermomyces, Thielavia, Tolypocladium, Trametes pleurotus, Trichoderma* and *Trichophyton*.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

The enzymatic hydrolysis of the integrated processes of the present invention are advantageously applied in combination with enzymes derived from a microorganism of the genus *Rasamsonia* or the enzymes used in the enzymatic hydrolysis of the integrated processes of the present invention comprise a *Rasamsonia* enzyme.

The enzymatic hydrolysis of the first stage is preferably done at 50-90° C. In this step thermostable cellulolytic enzymes are preferred. A "thermostable" enzyme as used herein means that the enzyme has a temperature optimum of 50° C. or higher, 60° C. or higher, 70° C. or higher, 75° C. or higher, 80° C. or higher, 85° C. or higher. They may for example be isolated from thermophilic microorganisms or may be designed by the skilled person and artificially synthesized. In one embodiment the polynucleotides may be isolated or obtained from thermophilic or thermotolerant filamentous fungi or isolated from non-thermophilic or non-thermotolerant fungi, but are found to be thermostable.

By "thermophilic fungus" is meant a fungus that grows at a temperature of 50° C. or higher. By "themotolerant" fungus is meant a fungus that grows at a temperature of 45° C. or higher, having a maximum near 50° C.

Suitable thermophilic or thermotolerant fungal cells may be a *Humicola, Rhizomucor, Myceliophthora, Rasamsonia, Talaromyces, Thermomyces, Thermoascus* or *Thielavia* cell, preferably a *Rasamsonia* cell. Preferred thermophilic or thermotolerant fungi are *Humicola grisea* var. *thermoidea, Humicola lanuginosa, Myceliophthora thermophila, Papulaspora thermophilia, Rasamsonia byssochlamydoides, Rasamsonia emersonii, Rasamsonia argillacea, Rasamsonia eburnean, Rasamsonia brevistipitata, Rasamsonia cylindrospora, Rhizomucor pusillus, Rhizomucor miehei, Talaromyces bacillisporus, Talaromyces leycettanus, Talaromyces thermophilus, Thermomyces lenuginosus, Thermoascus crustaceus, Thermoascus thermophilus Thermoascus aurantiacus* and *Thielavia terrestris*.

Thermophilic fungi are not restricted to a specific taxonomic order and occur all over the fungal tree of life. Examples are *Rhizomucor* in the Mucorales, *Myceliophthora* in Sordariales and *Talaromyces, Thermomyces* and *Thermoascus* in the Eurotiales (see Mouchacca, 1997). The majority of *Talaromyces* species are mesophiles, but exceptions are species within sections *Emersonii* and *Thermophila*. Section *Emersonii* includes *Talaromyces emersonii, Talaromyces byssochlamydoides, Talaromyces bacillisporus* and *Talaromyces leycettanus*, all of which grow well at 40° C. *Talaromyces bacillisporus* is thermotolerant, *Talaromyces leycettanus* is thermotolerant to thermophilic, and *Talaromyces emersonii* and *Talaromyces byssochlamydoides* are truly thermophilic (see Stolk and Samson, 1972). The sole member of *Talaromyces* section *Thermophila, Talaromyces thermophilus*, grows rapidly at 50° C. (see Stolk and Samson, 1972). The current classification of these thermophilic *Talaromyces* species is mainly based on phenotypic and physiological characters, such as their ability to grow above 40° C., ascospore color, the structure of ascornatal covering and the formation of a certain type of anamorph. Stolk and Samson (1972) stated that the members of the section *Emersonii* have anamorphs of either *Paecilomyces* (*Talaromyces byssochlamydoides* and *Talaromycesleycettanus*) or

*Penicillium cylindrosporum* series (*Talaromyces emersonii* and *Talaromyces bacillisporus*). Later, Pitt (1979) transferred the species belonging to the *Penicillium cylindrosporum* series to the genus *Geosmithia*, based on various characters such as the formation of conidia from terminal pores instead of on collula (necks), a character of *Penicillium* and *Paecilomyces*. Within the genus *Geosmithia*, only *Geosmithia argillacea* is thermotolerant, and Stolk et al. (1969) and Evans (1971) proposed a connection with members of *Talaromyces* sect. *Emersonii*. The phylogenetic relationship of the themophilic *Talaromyces* species within *Talaromyces* and the Trichocomaceae is unknown. (see J. Houbraken, Antonie van Leeuwenhoek 2012 February; 101 (2): 403-21).

*Rasamsonia* is a new genus comprising thermotolerant and thermophilic *Talaromyces* and *Geosmithia* species (J. Houbraken et al., vida supra). Based on phenotypic, physiological and molecular data, Houbraken et al. proposed to transfer the species *Talaromyces emersonii, Talaromyces byssochiamydoides, Talaromyces eburneus, Geosmithia argillacea* and *Geosmithia cylindrospora* to *Rasamsonia* gen. nov.

Preferred thermophilic fungi are *Rasamsonia byssochiamydoides, Rasamsonia emersonii, Thermomyces lenuginosus, Talaromyces thermophilus, Thermoascus crustaceus, Thermoascus thermophilus* and *Thermoascus aurantiacus*, with *Rasamsonia emersonii* being most preferred. *Talaromyces emersonii, Penicillium geosmithia emersonii* and *Rasamsonia emersonii* are used interchangeably herein.

Cellulolytic enzymes of *Rasamsonia* applied on pretreated lignocellulosic feedstock show maximal conversion rates at temperature within the range of 50 to 70° C. The enzymes remain active under these circumstances for 14 days and more without complete cessation of activity. By using optimal temperature conditions, a maximal amount of reducing sugars can be released from lignocellulosic material (total hydrolysis) within the shortest possible hydrolysis time. In this way, 100% conversion of cellulose in glucose can be achieved in less than 5 days. The theoretical maximum yield (Yps max in g product per gram glucose) of a fermentation product can be derived from textbook biochemistry. For ethanol, 1 mole of glucose (180 g) yields according to normal glycolysis fermentation pathway in yeast 2 moles of ethanol (=2×46=92 g ethanol). The theoretical maximum yield of ethanol on glucose is therefore 92/180=0.511 g ethanol/g glucose. For butanol (MW 74 g/mole) or isobutanol, the theoretical maximum yield is 1 mole of butanol per mole of glucose. So Yps max for (iso-)butanol=74/180=0.411 g (iso-)butanol/g glucose. For lactic acid the fermentation yield for homolactic fermentation is 2 moles of lactic acid (MW=90 g/mole) per mole of glucose. According to this stoichiometry, the Yps max=1 g lactic acid/g glucose. The theoretical maximum yield of succinic acid on glucose is 1.12 g succinic acid/g glucose. For other fermentation products a similar calculation may be made. The cost reduction achieved with applying cellulolytic enzymes of *Rasamsonia* are the result of an overall process time reduction.

Due to the high stability of the enzymes used in the processes of the present invention, it is possible to lower the enzyme dosage and extend the use of the enzyme by prolonging the hydrolysis times. For example, 0.175 mL enzyme/g lignocellulosic material dry matter results in release of approximately 90% of the theoretical maximum of reducing sugars from pretreated lignocellulosic material within 72 h. When using 0.075 mL enzyme/g lignocellulosic material dry matter, approximately 90% conversion of the theoretical maximum is achieved within 120 h. The results show that, because of the stability of the enzyme activity, lowering the enzyme dosage can be compensated by extending the hydrolysis time to obtain the same amount of reducing sugars. The cost reduction achieved by using stable cellulolytic enzymes, such as those of *Rasamsonia*, results in lower enzyme dosages that nevertheless result in similar hydrolysis conversion yields.

In a common process for converting lignocellulosic material into ethanol, process steps are preferably done under septic conditions to lower the operational costs. Contamination and growth of contaminating microorganisms can therefore occur and result in undesirable side effects, such as lactic acid, formic acid and acetic acid production, yield losses of ethanol on substrate, production of toxins and extracellular polysaccharides. These effects may affect production costs significantly. A high process temperature and/or a short process time limits the risk on contamination during hydrolysis and fermentation. Thermostable enzymes, like those of *Rasamsonia*, are capable of hydrolysing lignocellulosic material at temperatures of higher than 60° C. At these temperatures, the risk that a contaminating microorganism will cause undesired side effects is little to almost zero.

During the fermentation step, in which ethanol is produced, temperatures are typically between 30 to 38° C. and are preferably not raised because of production losses. By applying short fermentation process times, the risks and effects of contamination and/or growth of contaminants are reduced as much as possible. With stable enzymes, like those of *Rasamsonia*, a short fermentation time can be applied and thus risks of contamination and/or growth of contaminants are reduced as much as possible. The cost reduction achieved with applying thermostable cellulolytic enzymes of *Rasamsonia* in this way, results in a lower risk of process failures due to contamination.

The first step after thermal pretreatment is to cool the pretreated material to temperatures wherein the enzymes have an optimal activity. On large scale, this is typically done by adding (cooled) water, which, besides decreasing the temperature, reduces the dry matter content. By using thermostable enzymes, like those of *Rasamsonia*, cost reduction can be achieved, because (i) less cooling of the pretreated material is required since higher temperatures are allowed during hydrolysis, and (ii) less water is added, which increases the dry matter content during hydrolysis and fermentation and thus increase the ethanol production capacity (amount produced per time unit per volume) of an ethanol plant. By using thermostable enzymes, like those of *Rasamsonia*, cost reduction may also be achieved by using cooling water having a higher temperature than the water that is used in a process with non-thermostable enzyme.

At the end of the hydrolysis, enzyme activities appear to be low, since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, cantation, sedimentation, 60% or more (e.g. 70%) of the enzyme activity in solution can be recovered and re-used for hydrolysis of a new pretreated lignocellulosic material during the next hydrolysis. Moreover, after solid-liquid separation the enzyme in solution can be separated from the solution containing reducing sugars and other hydrolysis products from the enzymatic actions. This separation can be done by techniques including, but not limited to, ultra- and microfiltration, centrifugation, cantation, sedimentation, with or without first adsorption of the enzyme to a carrier of any kind. For example, after hydrolysis of pretreated material with 0.175 mL/g material dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60 to 70%. The cost reduction achieved by using stable cellulolytic enzymes, such as those of *Rasamsonia*, in this way is the consequence of a lower enzyme dosage.

The integrated processes of the present invention can be combined with enzyme recycling after hydrolysis, recycling of the ethanol producing microorganism after fermentation and/or recycling of the organic acid producing microorganism after fermentation and/or recycling of the enzyme producing microorganism after production of the enzymes.

The thermostability of enzymes, like those from *Rasamsonia*, causes remaining cellulolytic activity after hydrolysis, fermentation and vacuum distillation in the thin stillage. The total activity of the enzyme is reduced during the three successive process steps. The thin stillage obtained after vacuum distillation can thus be re-used as a source of enzyme for a newly started hydrolysis-fermentation-distillation process cycle of pretreated material conversion into ethanol. The thin stillage can be used either in concentrated or (un)diluted form and/or purified and with or without additional enzyme supplementation.

In an optimal process, an amount of enzyme is supplemented into the thin stillage, before its re-use in a new process cycle, equal to the amount of activity lost during the three successive process steps of the previous process cycle. In this way over dosage of enzyme is avoided and thus most efficient use of enzyme is obtained. Moreover, by providing high enzyme dosage in the first process cycle, and supplementing enzyme equal to the amount of activity lost during the three successive process steps in the following process cycles, highest possible hydrolysis rates can be obtained in each process cycle resulting in short hydrolysis times of less than 48 h in combination with most efficient use of enzymes.

By applying mixing during hydrolysis, enzymes come more often in contact with substrates, which results in a more efficient use of the catalytic activity. This will result in a lower enzyme dosages and thus in lower costs, unless the mixing has a negative effect on the enzymes. Stable enzymes, like the thermostable enzymes from *Rasamsonia*, are robust and can resist circumstances of (locally) high shear and temperatures, which is the case during intensive mixing of slurries. The use of them in mixed systems is therefore beneficial and will lead to dosage and thus costs reduction.

An advantage of expression and production of the enzymes (for example at least two, three or four different cellulases) in a suitable microorganism may be a high enzyme composition yield which can be used in the processes of the present invention.

In the processes of the present invention enzyme compositions are used. Preferably, the compositions are stable. "Stable enzyme compositions" as used herein means that the enzyme compositions retain activity after 30 hours of hydrolysis reaction time, preferably at least 10%, 20%, 30%, 40%, 50%, 60%, 65%, 70%, 75%, 80% 85%, 90%, 95%, 96%, 97%, 98%, 99% or 100% of its initial activity after 30 hours of hydrolysis reaction time. Preferably, the enzyme composition retains activity after 40, 50, 60, 70, 80, 90 100, 150, 200, 250, 300, 350, 400, 450, 500 hours of hydrolysis reaction time.

The enzymes may be prepared by fermentation of a suitable substrate with a suitable microorganism, e.g. *Rasamsonia emersonii* or *Aspergillus niger*, wherein the enzymes are produced by the microorganism. The microorganism may be altered to improve or to make the enzymes. For example, the microorganism may be mutated by classical strain improvement procedures or by recombinant DNA techniques. Therefore, the microorganisms mentioned herein can be used as such to produce the enzymes or may be altered to increase the production or to produce altered enzymes which might include heterologous enzymes, e.g. cellulases, thus enzymes that are not originally produced by that microorganism. Preferably, a fungus, more preferably a filamentous fungus is used to produce the enzymes. Advantageously, a thermophilic or thermotolerant microorganism is used. Optionally, a substrate is used that induces the expression of the enzymes by the enzyme producing microorganism.

The enzymes are used to release sugars from lignocellulosic material, that comprises polysaccharides. The major polysaccharides are cellulose (glucans), hemicelluloses (xylans, heteroxylans and xyloglucans). In addition, some hemicellulose may be present as glucomannans, for example in wood-derived lignocellulosic material. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. By sugar product is meant the enzymatic hydrolysis product of the lignocellulosic material. The sugar product comprises soluble sugars, including both monomers and multimers. Preferably, it comprises glucose. Examples of other sugars are cellobiose, xylose, arabinose, galactose, fructose, mannose, rhamnose, ribose, galacturonic acid, glucuronic acid and other hexoses and pentoses. The sugar product may be used as such or may be further processed, for example recovered, concentrated and/or purified.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to a) generates structures more prone to inter strand hydrogen bonding than the highly branched α-linked structures of starch. Thus, cellulose polymers are generally less soluble and form more tightly bound fibers than the fibers found in starch.

Enzymes that may be used in the invention are described in more detail below.

Lytic polysaccharide monooxygenases, endoglucanases (EG) and exo-cellobiohydrolases (CBH) catalyze the hydrolysis of insoluble cellulose to products such as cellooligosaccharides (cellobiose as a main product), while β-glucosidases (BG) convert the oligosaccharides, mainly cellobiose and cellotriose, to glucose.

Hemicellulose is a complex polymer, and its composition often varies widely from organism to organism and from one tissue type to another. In general, a main component of hemicellulose is β-1,4-linked xylose, a five carbon sugar. However, this xylose is often branched at 0 to 3 and/or 0 to 2 atoms of xylose, and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Xylanases together with other accessory enzymes, for example α-L-arabinofuranosidases, feruloyl and acetylxylan esterases, glucuronidases, and β-xylosidases) catalyze the hydrolysis of hemicellulose.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another. The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

Enzymes for use in the integrated processes of the current invention comprise preferably at least two activities, although typically enzymes will comprise more than two activities, for example, three, four, five, six, seven, eight, nine or even more activities. Typically, enzymes for use in the integrated processes of the current invention comprise at least two cellulases. The at least two cellulases may contain the same or different activities. Enzymes for use in the integrated processes of the current invention may also comprises at least one enzyme other than a cellulase. Preferably, the at least one other enzyme has an auxiliary enzyme activity, i.e. an additional activity which, either directly or indirectly leads to lignocellulose degradation. Examples of such auxiliary activities are mentioned herein and include, but are not limited to hemicellulases.

Thus, enzymes for use in the integrated processes of the current invention may comprise lytic polysaccharide monooxygenase activity, endoglucanase activity and/or cellobiohydrolase activity and/or beta-glucosidase activity. Enzymes for use in the invention may comprise more than one enzyme activity per activity class. For example, enzymes for use in the invention may comprise two endoglucanase activities, for example, endo-1,3(1,4)-β glucanase activity and endo-β-1,4-glucanase activity.

Enzymes for use in the integrated processes of the current invention may be derived from a fungus, such as a filamentous fungus such as Rasamsonia, such as Rasamsonia emersonii. In an embodiment a core set of (lignocellulose degrading) enzyme activities may be derived from Rasamsonia emersonii. Rasamsonia emersonii can provide a highly effective set of activities as demonstrated herein for the hydrolysis of lignocellulosic material. If needed, the set of activities can be supplemented with additional enzyme activities from other sources. Such additional activities may be derived from classical sources and/or produced by a genetically modified organisms.

The enzyme activities for use in the integrated processes of the current invention may be thermostable. Herein, this means that the activity has a temperature optimum of 60° C. or higher, 70° C. or higher, 75° C. or higher, 80° C. or higher, 85° C. or higher. Activities for use in the integrated processes of the current invention will typically not have the same temperature optima, but preferably will, nevertheless, be thermostable.

In addition, enzyme activities for use in the integrated processes of the current invention may be able to work at low pH. For the purposes of this invention, low pH indicates a pH of 5.5 or lower, 5 or lower, 4.9 or lower, 4.8 or lower, 4.7 or lower, 4.6 or lower, 4.5 or lower, 4.4 or lower, 4.3 or lower, 4.2 or lower, 4.1 or lower, 4.0 or lower 3.9 or lower, 3.8 or lower, 3.7 or lower, 3.6 or lower, 3.5 or lower.

Activities for use in the integrated processes of the current invention may be defined by a combination of any of the above temperature optima and pH values.

Enzymes for use in the integrated processes of the current invention may comprise a cellulase and/or a hemicellulase and/or a pectinase from a source other than Rasamsonia. They may be used together with one or more Rasamsonia enzymes or they may be used without additional Rasamsonia enzymes being present.

For example, enzymes for use in the integrated processes of the current invention may comprise a beta-glucosidase (BG) from Aspergillus, such as Aspergillus oryzae, such as the one disclosed in WO 02/095014 or the fusion protein having beta-glucosidase activity disclosed in WO 2008/057637, or Aspergillus fumigatus, such as the one disclosed as SEQ ID NO:2 in WO 2005/047499 or SEQ ID NO:5 in WO 2014/130812 or an Aspergillus fumigatus beta-glucosidase variant, such as one disclosed in WO 2012/044915, such as one with the following substitutions: F100D, S283G, N456E, F512Y (using SEQ ID NO: 5 in WO 2014/130812 for numbering), or Aspergillus aculeatus, Aspergillus niger or Aspergillus kawachi. In another embodiment the beta-glucosidase is derived from Penicillium, such as Penicillium brasilianum disclosed as SEQ ID NO:2 in WO 2007/019442, or from Trichoderma, such as Trichoderma reesei, such as ones described in U.S. Pat. Nos. 6,022,725, 6,982, 159, 7,045,332, 7,005,289, US 2006/0258554 US 2004/0102619. In an embodiment even a bacterial beta-glucosidase can be used. In another embodiment the beta-glucosidase is derived from Thielavia terrestris (WO 2011/035029) or Trichophaea saccata (WO 2007/019442).

For example, enzymes for use in the integrated processes of the current invention may comprise an endoglucanase (EG) from Trichoderma, such as Trichoderma reesei; from Humicola, such as a strain of Humicola insolens; from Aspergillus, such as Aspergillus aculeatus or Aspergillus kawachii; from Erwinia, such as Erwinia carotovara; from Fusarium, such as Fusarium oxysporum; from Thielavia, such as Thielavia terrestris; from Humicola, such as Humicola grisea var. thermoidea or Humicola insolens; from Melanocarpus, such as Melanocarpus albomyces; from Neurospora, such as Neurospora crassa; from Myceliophthora, such as Myceliophthora thermophila; from Cladorrhinum, such as Cladorrhinum foecundissimum and/or from Chrysosporium, such as a strain of Chrysosporium lucknowense. In an embodiment even a bacterial endoglucanase can be used including, but are not limited to, *Acidothermus cellulolyticus* endoglucanase (see WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (see WO 05/093050); and *Thermobifida fusca* endoglucanase V (see WO 05/093050).

For example, enzymes for use in the integrated processes of the current invention may comprise a cellobiohydrolase I from *Aspergillus*, such as *Aspergillus fumigatus*, such as the Cel7A CBH I disclosed in SEQ ID NO:6 in WO 2011/057140 or SEQ ID NO:6 in WO 2014/130812, or from *Trichoderma*, such as *Trichoderma reesei*.

For example, enzymes for use in the integrated processes of the current invention may comprise a cellobiohydrolase II from *Aspergillus*, such as *Aspergillus fumigatus*, such as the one in SEQ ID NO:7 in WO 2014/130812 or from *Trichoderma*, such as *Trichoderma reesei*, or from *Thielavia*, such as *Thielavia terrestris*, such as cellobiohydrolase II CEL6A from *Thielavia terrestris*.

For example, enzymes for use in the integrated processes of the current invention may comprise a GH61 polypeptide (a lytic polysaccharide monooxygenase) from *Thermoascus*, such as *Thermoascus aurantiacus*, such as the one described in WO 2005/074656 as SEQ ID NO:2 and SEQ ID NO:1 in WO2014/130812 and in WO 2010/065830; or from *Thielavia*, such as *Thielavia terrestris*, such as the one described in WO 2005/074647 as SEQ ID NO: 8 or SEQ ID NO:4 in WO2014/130812 and in WO 2008/148131, and WO 2011/035027; or from *Aspergillus*, such as *Aspergillus fumigatus*, such as the one described in WO 2010/138754 as SEQ ID NO:2 or SEQ ID NO: 3 in WO2014/130812; or from *Penicillium*, such as *Penicillium emersonii*, such as the one disclosed as SEQ ID NO:2 in WO 2011/041397 or SEQ ID NO:2 in WO2014/130812. Other suitable GH61 polypeptides include, but are not limited to, *Trichoderma reesei* (see WO 2007/089290), *Myceliophthora thermophila* (see WO 2009/085935, WO 2009/085859, WO 2009/085864, WO 2009/085868), *Penicillium pinophilum* (see WO 2011/005867), *Thermoascus* sp. (see WO 2011/039319), and *Thermoascus crustaceous* (see WO 2011/041504). In one aspect, the GH61 polypeptide is used in the presence of a soluble activating divalent metal cation according to WO 2008/151043, e.g. manganese sulfate. In one aspect, the GH61 polypeptide is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover.

Other cellulolytic enzymes that may be used in the integrated processes of the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593, to name just a few.

In addition, examples of xylanases useful in the integrated processes of the present invention include, but are not limited to, xylanases from *Aspergillus aculeatus* (see WO 94/21785), *Aspergillus fumigatus* (see WO 2006/078256), *Penicillium pinophilum* (see WO 2011/041405), *Penicillium* sp. (see WO 2010/126772), *Thielavia terrestris* NRRL 8126 (see WO 2009/079210), and *Trichophaea saccata* GH10 (see WO 2011/057083). Examples of beta-xylosidases useful in the integrated processes of the present invention include, but are not limited to, beta-xylosidases from *Neurospora crassa* and *Trichoderma reesei*. Examples of acetylxylan esterases useful in the processes of the present invention include, but are not limited to, acetylxylan esterases from *Aspergillus aculeatus* (see WO 2010/108918), *Chaetomium globosum*, *Chaetomium gracile*, *Humicola insolens* DSM 1800 (see WO 2009/073709), *Hypocrea jecorina* (see WO 2005/001036), *Myceliophtera thermophila* (see WO 2010/014880), *Neurospora crassa*, *Phaeosphaeria nodorum* and *Thielavia terrestris* NRRL 8126 (see WO 2009/042846). Examples of feruloyl esterases (ferulic acid esterases) useful in the integrated processes of the present invention include, but are not limited to, feruloyl esterases form *Humicola insolens* DSM 1800 (see WO 2009/076122), *Neosartorya fischeri*, *Neurospora crassa*, *Penicillium aurantiogriseum* (see WO 2009/127729), and *Thielavia terrestris* (see WO 2010/053838 and WO 2010/065448). Examples of arabinofuranosidases useful in the integrated processes of the present invention include, but are not limited to, arabinofuranosidases from *Aspergillus niger*, *Humicola insolens* DSM 1800 (see WO 2006/114094 and WO 2009/073383) and *M. giganteus* (see WO 2006/114094). Examples of alpha-glucuronidases useful in the processes of the present invention include, but are not limited to, alpha-glucuronidases from *Aspergillus clavatus*, *Aspergillus fumigatus*, *Aspergillus niger*, *Aspergillus terreus*, *Humicola insolens* (see WO 2010/014706), *Penicillium aurantiogriseum* (see WO 2009/068565) and *Trichoderma reesei*.

Enzymes for use in the integrated processes of the current invention may comprise one, two, three, four classes or more of cellulase, for example one, two, three or four or all of a lytic polysaccharide monooxygenas (LPMO), an endoglucanase (EG), one or two exo-cellobiohydrolase (CBH) and a beta-glucosidase (BG). Enzymes for use in the integrated processes of the current invention may comprise two or more of any of these classes of cellulase.

Enzymes for use in the integrated processes of the current invention may comprise one type of cellulase activity and/or hemicellulase activity and/or pectinase activity provided by enzymes as described herein and a second type of cellulase activity and/or hemicellulase activity and/or pectinase activity provided by an additional cellulase/hemicellulase/pectinase.

As used herein, a cellulase is any polypeptide which is capable of degrading or modifying cellulose. A polypeptide which is capable of degrading cellulose is one which is capable of catalyzing the process of breaking down cellulose into smaller units, either partially, for example into cellodextrins, or completely into glucose monomers. A cellulase according to the invention may give rise to a mixed population of cellodextrins and glucose monomers. Such degradation will typically take place by way of a hydrolysis reaction.

Lytic polysaccharide monooxygenases (LPMO) are recently classified by CAZy in family AA9 (Auxiliary Activity Family 9) or family AA10 (Auxiliary Activity Family 10). As mentioned above, lytic polysaccharide monooxygenases are able to open a crystalline glucan structure. Lytic polysaccharide monooxygenases may also affect cello-oligosaccharides. GH61 (glycoside hydrolase family 61 or sometimes referred to EGIV) proteins are (lytic) oxygen-dependent polysaccharide monooxygenases (PMO's/LPMO's) according to the latest literature (see Isaksen et al., Journal of Biological Chemistry, vol. 289, no.

5, pp. 2632-2642). PMO and LPMO are used herein interchangeably. Often in literature these proteins are mentioned to enhance the action of cellulases on lignocellulose substrates. GH61 was originally classified as endoglucanase based on measurement of very weak endo-1,4-β-d-glucanase activity in one family member. The term "GH61" as used herein, is to be understood as a family of enzymes, which share common conserved sequence portions and folding to be classified in family 61 of the well-established CAZy GH classification system (www.cazy.org/GH61.html). The glycoside hydrolase family 61 is a member of the family of glycoside hydrolases EC 3.2.1. GH61 are recently now reclassified by CAZy in family AA9 (Auxiliary Activity Family 9). GH61 is used herein as being part of the cellulases.

CBM33 (family 33 carbohydrate-binding module) is a lytic polysaccharide monooxygenase (see Isaksen et al, Journal of Biological Chemistry, vol. 289, no. 5, pp. 2632-2642), CAZy has recently reclassified CBM33 in AA10 (Auxiliary Activity Family 10).

As used herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalyzing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers. Such degradation will typically take place by way of a hydrolysis reaction.

As used herein, a pectinase is any polypeptide which is capable of degrading or modifying pectin. A polypeptide which is capable of degrading pectin is one which is capable of catalyzing the process of breaking down pectin into smaller units, either partially, for example into oligosaccharides, or completely into sugar monomers. A pectinase according to the invention may give rise to a mixed population of oligosacchardies and sugar monomers. Such degradation will typically take place by way of a hydrolysis reaction.

Accordingly, enzymes for use in the integrated processes of the current invention may comprise any cellulase, for example, a lytic polysaccharide monooxygenase (e.g. GH61), a cellobiohydrolase, an endo-β-1,4-glucanase, a beta-glucosidaseor a β-(1,3)(1,4)-glucanase.

As used herein, a cellobiohydrolase (EC 3.2.1.91) is any polypeptide which is capable of catalyzing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

As used herein, an endo-β-1,4-glucanase (EC 3.2.1.4) is any polypeptide which is capable of catalyzing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

As used herein, a beta-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanse when the glucose residue whose reducing group is involved in the linkage to be hydrolysed is itself substituted at C-3. Alternative names include endo-1,3-beta-glucanase, laminarinase, 1,3-(1,3;1, 4)-beta-D-glucan 3 (4) glucanohydrolase. Substrates include laminarin, lichenin and cereal beta-D-glucans.

Enzymes for use in the integrated processes of the current invention may comprise any hemicellulase, for example, an endoxylanase, a β-xylosidase, a α-L-arabionofuranosidase, an α-D-glucuronidase, an acetyl xylan esterase, a feruloyl esterase, a coumaroyl esterase, an α-galactosidase, a β-galactosidase, a β-mannanase or a β-mannosidase.

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

As used herein, a β-xylosidase (EC 3.2.1.37) is any polypeptide which is capable of catalysing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

As used herein, a feruloyl esterase (EC 3.1.1.73) is any polypeptide which is capable of catalysing a reaction of the form: feruloyl-saccharide+$H_2O$=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

Enzymes for use in the integrated processes of the current invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n $H_2O$=n methanol+pectate. The enzyme may also been known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1-4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: (1,4-α-D-galacturonide)$_n$+$H_2O$=(1,4-α-D-galacturonide)$_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the p-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

Enzymes for use in the integrated processes of the current invention will typically comprise at least two cellulases and optionally at least one hemicellulase and optionally at least one pectinase. Enzymes for use in the integrated processes of the current invention may comprise a lytic polysaccharide monooxygenases (such as GH61), a cellobiohydrolase, an endoglucanase and/or a beta-glucosidase. Such enzymes may also comprise one or more hemicellulases and/or one or more pectinases.

In addition, one or more (for example two, three, four or all) of an amylase, a protease, a lipase, a ligninase, a hexosyltransferase, a glucuronidase, an expansin, a cellulose induced protein or a cellulose integrating protein or like protein may be present in the enzymes for use in the integrated processes of the current invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes of the current invention. Some specific types of proteases include, cysteine proteases including pepsin, papain and serine proteases including chymotrypsins, carboxypeptidases and metal loendopeptidases.

"Lipase" includes enzymes that hydrolyze lipids, fatty acids, and acylglycerides, including phospoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

Enzymes for use in the integrated processes of the current invention may comprise an expansin or expansin-like protein, such as a swollenin (see Salheimo et al., Eur. J. Biochem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

Enzymes for use in the integrated processes of the current invention may comprise a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multifunctional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

Enzymes for use in the integrated processes of the current invention may also comprise a catalase. The term "catalase" means a hydrogen-peroxide: hydrogen-peroxide oxidoreductase (EC 1.11.1.6 or EC 1.11.1.21) that catalyzes the conversion of two hydrogen peroxides to oxygen and two waters. Catalase activity can be determined by monitoring the degradation of hydrogen peroxide at 240 nm based on the following reaction: $2H_2O_2 \rightarrow 2H_2O+O_2$. The reaction is conducted in 50 mM phosphate pH 7.0 at 25° C. with 10.3 mM substrate ($H_2O_2$) and approximately 100 units of enzyme per ml. Absorbance is monitored spectrophotometrically within 16-24 seconds, which should correspond to an absorbance reduction from 0.45 to 0.4. One catalase activity unit can be expressed as one micromole of $H_2O_2$ degraded per minute at pH 7.0 and 25° C.

Enzymes for use in the integrated processes of the current invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

Enzymes for use in the integrated processes of the current invention may be composed of enzymes from (1) commercial suppliers; (2) cloned genes expressing enzymes; (3) broth (such as that resulting from growth of a microbial strain in media, wherein the strains secrete proteins and enzymes into the media; (4) cell lysates of strains grown as in (3); and/or (5) plant material expressing enzymes. Different enzymes may be obtained from different sources.

The enzymes can be produced either exogenously in microorganisms, yeasts, fungi, bacteria or plants, then isolated and added, for example, to (pretreated) lignocellulosic material. Alternatively, the enzyme may be produced in a fermentation that uses (pretreated) lignocellulosic material (such as corn stover or wheat straw) to provide nutrition to an organism that produces an enzyme(s). In this manner, plants that produce the enzymes may themselves serve as a lignocellulosic material and be added into lignocellulosic material.

In the uses and processes described herein, the enzymes described above may be provided concomitantly (i.e. in a single composition of enzymes) or separately or sequentially.

In an embodiment the enzymes are in the form of a whole fermentation broth. The whole fermentation broth can be prepared from fermentation of non-recombinant and/or recombinant filamentous fungi. In an embodiment the filamentous fungus is a recombinant filamentous fungus comprising one or more genes which can be homologous or heterologous to the filamentous fungus. In an embodiment, the filamentous fungus is a recombinant filamentous fungus comprising one or more genes which can be homologous or heterologous to the filamentous fungus wherein the one or more genes encode enzymes that can degrade a cellulosic substrate. The whole fermentation broth may comprise any of the polypeptides or any combination thereof.

Preferably, the composition of enzymes is whole fermentation broth wherein the cells are killed. The whole fermentation broth may contain organic acid(s) (used for killing the cells), killed cells and/or cell debris, and culture medium.

Generally, the filamentous fungi is cultivated in a cell culture medium suitable for production of enzymes capable of hydrolyzing a cellulosic substrate. The cultivation takes place in a suitable nutrient medium comprising carbon and nitrogen sources and inorganic salts, using procedures known in the art. Suitable culture media, temperature ranges and other conditions suitable for growth and cellulase and/or hemicellulase and/or pectinase production are known in the art. The whole fermentation broth can be prepared by growing the filamentous fungi to stationary phase and maintaining the filamentous fungi under limiting carbon conditions for a period of time sufficient to express the one or more cellulases and/or hemicellulases and/or pectinases. Once enzymes, such as cellulases and/or hemicellulases and/or pectinases, are secreted by the filamentous fungi into the fermentation medium, the whole fermentation broth can be used. The whole fermentation broth of the present invention may comprise filamentous fungi. In some embodiments, the whole fermentation broth comprises the unfractionated contents of the fermentation materials derived at the end of the fermentation. Typically, the whole fermentation broth comprises the spent culture medium and cell debris present after the filamentous fungi is grown to saturation, incubated under carbon-limiting conditions to allow protein synthesis (particularly, expression of cellulases and/or hemicellulases and/or pectinases). In some embodiments, the whole fermentation broth comprises the spent cell culture medium, extracellular enzymes and filamentous fungi. In some embodiments, the filamentous fungi present in whole fermentation broth can be lysed, permeabilized, or killed using methods known in the art to produce a cell-killed whole fermentation broth. In an embodiment, the whole fermentation broth is a cell-killed whole fermentation broth, wherein the whole fermentation broth containing the filamentous fungi cells are lysed or killed. In some embodiments, the cells are killed by lysing the filamentous fungi by chemical and/or pH treatment to generate the cell-killed whole broth of a fermentation of the filamentous fungi. In some embodiments, the cells are killed by lysing the filamentous fungi by chemical and/or pH treatment and adjusting the pH of the cell-killed fermentation mix to a suitable pH. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably non-viable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or anti-microbial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

In an embodiment, the whole fermentation broth may be supplemented with one or more enzyme activities that are not expressed endogenously, or expressed at relatively low level by the filamentous fungi, to improve the degradation of the cellulosic substrate, for example, to fermentable sugars such as glucose or xylose. The supplemental enzyme(s) can be added as a supplement to the whole fermentation broth and the enzymes may be a component of a separate whole fermentation broth, or may be purified, or minimally recovered and/or purified.

In an embodiment, the whole fermentation broth comprises a whole fermentation broth of a fermentation of a recombinant filamentous fungi overexpressing one or more enzymes to improve the degradation of the cellulosic substrate. Alternatively, the whole fermentation broth can comprise a mixture of a whole fermentation broth of a fermentation of a non-recombinant filamentous fungus and a recombinant filamentous fungus overexpressing one or more enzymes to improve the degradation of the cellulosic substrate. In an embodiment, the whole fermentation broth comprises a whole fermentation broth of a fermentation of a filamentous fungi overexpressing beta-glucosidase. Alternatively, the whole fermentation broth for use in the present methods and reactive compositions can comprise a mixture of a whole fermentation broth of a fermentation of a non-recombinant filamentous fungus and a whole fermentation broth of a fermentation of a recombinant filamentous fungi overexpressing a beta-glucosidase.

Enzymes are present in the liquefaction step and in the saccharification step of the enzymatic hydrolysis. These enzymes may be the same or may be different. Furthermore, as described above, additional enzymes are added during the liquefaction step and the saccharification step of the integrated processes according to the present invention. The enzymes added may be enzymes that are already present in the liquefaction step and in the saccharification step. Alternatively, they may be different enzymes. Moreover, the additional enzymes added during the liquefaction step may differ or may be the same as the additional enzymes added during the saccharification step of the integrated processes according to the present invention.

Lignocellulosic material as used herein includes any lignocellulosic and/or hemicellulosic material. Lignocellulosic material suitable for use in the processes of the current invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane, cane straw, sugar cane bagasse, switch grass, *miscanthus*, energy cane, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof. In a preferred embodiment the lignocellulosic material is sugar cane bagasse or sugar cane straw.

Cellulose is an organic compound with the formula $(C_6H_{10}O_5)_n$, a polysaccharide consisting of a linear chain of several hundred to over ten thousand $\beta(1 \rightarrow 4)$ linked D-glucose units. A glucan molecule is a polysaccharide of D-glucose monomers linked by glycosidic bonds. Herein glucan and cellulose are used interchangeably for a polysaccharide of D-glucose monomers linked by glycosidic bonds. Methods for the quantitative analysis of glucan or polysaccharide compositions are well-known and described in the art and are for example summarized in Carvalho de Souza et al., Carbohydrate Polymers 95 (2013) 657-663. In general, 50 to 70% of the glucan is crystalline cellulose, the remainder is amorphous cellulose.

In an embodiment the lignocellulosic material is pretreated before and/or during the enzymatic hydrolysis. Pretreatment methods are known in the art and include, but are not limited to, heat, mechanical, chemical modification, biological modification and any combination thereof. Pretreatment is typically performed in order to enhance the accessibility of the lignocellulosic material to enzymatic hydrolysis and/or hydrolyse the hemicellulose and/or solubilize the hemicellulose and/or cellulose and/or lignin, in the lignocellulosic material. In an embodiment, the pretreatment comprises treating the lignocellulosic material with steam explosion, hot water treatment or treatment with dilute acid or dilute base. Examples of pretreatment methods include, but are not limited to, steam treatment (e.g. treatment at 100-260° C., at a pressure of 7-45 bar, at neutral pH, for 1-10 minutes), dilute acid treatment (e.g. treatment with 0.1-5% $H_2SO_4$ and/or $SO_2$ and/or $HNO_3$ and/or HCl, in presence or absence of steam, at 120-200° C., at a pressure of 2-15 bar, at acidic pH, for 2-30 minutes), organosolv treatment (e.g. treatment with 1-1.5% $H_2SO_4$ in presence of organic solvent and steam, at 160-200° C., at a pressure of 7-30 bar, at acidic pH, for 30-60 minutes), lime treatment (e.g. treatment with 0.1-2% $NaOH/Ca(OH)_2$ in the presence of water/steam at 60-160° C., at a pressure of 1-10 bar, at alkaline pH, for 60-4800 minutes), ARP treatment (e.g. treatment with 5-15% $NH_3$, at 150-180° C., at a pressure of 9-17 bar, at alkaline pH, for 10-90 minutes), AFEX treatment (e.g. treatment with >15% $NH_3$, at 60-140° C., at a pressure of 8-20 bar, at alkaline pH, for 5-30 minutes).

The lignocellulosic material may be washed. In an embodiment the lignocellulosic material may be washed before and/or after the pretreatment. The washing step may be performed before and/or after solid/liquid separation of the lignocellulosic material and/or the pretreated lignocellulosic material. If performed after the solid/liquid separation, the solid fraction obtained after solid/liquid separation may be washed. The washing step may be used to remove water soluble compounds that may act as inhibitors for the fermentation and/or hydrolysis step. The washing step may be conducted in manner known to the skilled person. Next to washing, other detoxification methods do exist. The pretreated lignocellulosic material may also be detoxified by any (or any combination) of these methods which include, but are not limited to, solid/liquid separation, vacuum evaporation, extraction, adsorption, neutralization, overliming, addition of reducing agents, addition of detoxifying enzymes such as laccases or peroxidases, addition of microorganisms capable of detoxification of hydrolysates.

The enzymes used in the integrated processes of the invention can extremely effectively hydrolyze lignocellulosic material, for example corn stover, wheat straw, cane straw, and/or sugar cane bagasse, which can then be further converted into a product, such as ethanol, biogas, butanol, a plastic, an organic acid such as succinic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials. The present invention is exemplified with the production of ethanol and succinic acid, but this is done as exemplification only rather than as limitation, the other products mentioned can be produced equally well.

In an embodiment the amount of enzyme added (herein also called enzyme dosage or enzyme load) is low. In an embodiment the amount of enzyme is 10 mg protein/g dry matter weight or lower, 9 mg protein/g dry matter weight or lower, 8 mg protein/g dry matter weight or lower, 7 mg protein/g dry matter weight or lower, 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 5 mg enzyme/g dry matter weight or lower, 4 mg enzyme/g dry matter weight or lower, 3 mg enzyme/g dry matter weight or lower, 2 mg enzyme/g dry matter weight or lower, 1 mg enzyme/g dry matter weight or lower, 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). A low enzyme dosage is possible, because of the activity and stability of the enzymes. When the enzymatic hydrolysis comprises a separate liquefaction step and a saccharification step, enzyme may be added before and/or during only one of the steps or before and/or during both steps.

The pH during the enzymatic hydrolysis may be chosen by the skilled person. In an embodiment the pH during the hydrolysis may be 3.0 to 6.4. The stable enzymes of the invention may have a broad pH range of up to 2 pH units, up to 3 pH units, up to 5 pH units. The optimum pH may lie within the limits of pH 2.0 to 8.0, 2.5 to 7.5, 3.0 to 7.0, 3.5 to 6.5, 4.0 to 5.0, 4.0 to 4.5 or is about 4.2. The pH used in the liquefaction step of the enzymatic hydrolysis and the saccharification step of the enzymatic hydrolysis may differ or may be the same. In case different enzymes are used during the liquefaction step and the saccharification step, the optimum pH of said enzymes may differ or may be the same.

In an embodiment the hydrolysis step is conducted until 70% or more, 80% or more, 85% or more, 90% or more, 92% or more, 95% or more of available sugar in the lignocellulosic material is released.

Significantly, a process of the invention may be carried out using high levels of dry matter (of the lignocellulosic material) in the hydrolysis reaction. In an embodiment the dry matter content at the end of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the liquefaction step of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the liquefaction step of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the dry matter content at the end of the saccharification step of the enzymatic hydrolysis is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher or 39 wt % or higher. In an embodiment the dry matter content at the end of the saccharification step of the enzymatic hydrolysis is between 5 wt %-40 wt %, 6 wt %-40 wt %, 7 wt %-40 wt %, 8 wt %-40 wt %, 9 wt %-40 wt %, 10 wt %-40 wt %, 11 wt %-40 wt %, 12 wt %-40 wt %, 13 wt %-40 wt %, 14 wt %-40 wt %, 15 wt %-40 wt %, 16 wt %-40 wt %, 17 wt %-40 wt %, 18 wt %-40 wt %, 19 wt %-40 wt %, 20 wt %-40 wt %, 21 wt %-40 wt %, 22 wt %-40 wt %, 23 wt %-40 wt %, 24 wt %-40 wt %, 25 wt %-40 wt %, 26 wt %-40 wt %, 27 wt %-40 wt %, 28 wt %-40 wt %, 29 wt %-40 wt %, 30 wt %-40 wt %, 31 wt %-40 wt %, 32 wt %-40 wt %, 33 wt %-40 wt %, 34 wt %-40 wt %, 35 wt %-40 wt %, 36 wt %-40 wt %, 37 wt %-40 wt %, 38 wt %-40 wt %, 39 wt %-40 wt %.

In an embodiment the fermentation steps in the integrated processes according to the present invention are performed in one or more containers. In an embodiment the fermentation of the at least solid fraction and/or the at least liquid fraction by an alcohol producing microorganism to produce alcohol is performed in one or more containers. In an embodiment the fermentation of the at least liquid fraction and/or the at least solid fraction by an organic acid producing microorganism to produce an organic acid is performed in one or more containers. The fermentation of the at least solid fraction and/or the at least liquid fraction by an alcohol producing microorganism to produce alcohol can be done in the same container(s) wherein the enzymatic hydrolysis is performed. Alternatively, the fermentation of the at least solid fraction and/or the at least liquid fraction by an alcohol producing microorganism to produce alcohol and the fermentation of the at least liquid fraction and/or the at least solid fraction by an organic acid producing microorganism to produce an organic acid can be performed in one or more separate containers, but may also be done in one or more of the same containers.

In an embodiment the alcohol producing microorganism is able to ferment at least a C5 sugar and at least a C6 sugar. In an embodiment the organic acid producing microorganism is able to ferment at least a C6 sugar. In an embodiment the alcohol producing microorganism and the organic acid producing microorganism are different microorganisms. In another embodiment the alcohol producing microorganism and the organic acid producing microorganism are the same microorganism, i.e. the alcohol producing microorganism is also able to produce organic acid such as succinic acid. In an embodiment the alcohol producing microorganism and/or the organic acid producing microorganism is a yeast.

In a further aspect, the invention thus includes fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrates (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic material (e.g. 50 g/l xylose, 35 g/l L-arabinose and 10 g/l galactose). For more dilute sugar compositions, the fermentation time may correspondingly be reduced. In an embodiment the fermentation time of the ethanol production step is between 10 and 50 hours for ethanol made out of C6 sugars and between 20 and 100 hours for ethanol made out of C5 sugars. In an embodiment the fermentation time of the succinic acid production step is between 20 and 70 hours.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a β-lactam antibiotics and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

In an embodiment the alcohol fermentation process is anaerobic, while the organic acid fermentation process is aerobic, but done under oxygen-limited conditions.

The fermentation process is preferably run at a temperature that is optimal for the modified cell. Thus, for most yeasts or fungal cells, the fermentation process is performed at a temperature which is less than 42° C., preferably 38° C.

or lower. For yeast or filamentous fungal host cells, the fermentation process is preferably performed at a temperature which is lower than 35, 33, 30 or 28° C. and at a temperature which is higher than 20, 22, or 25° C. In an embodiment the alcohol fermentation step and the organic acid fermentation step are performed between 25° C. and 35° C.

In an embodiment of the invention, the fermentations are conducted with a fermenting microorganism. In an embodiment of the invention, the alcohol (e.g. ethanol) fermentations of C5 sugars are conducted with a C5 fermenting microorganism. In an embodiment of the invention, the alcohol (e.g. ethanol) fermentations of C6 sugars are conducted with a C5 fermenting microorganism or a commercial C6 fermenting microorganism. Commercially available yeast suitable for ethanol production include, but are not limited to, BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA). In an embodiment the fermentations are performed in one or more containers. In an embodiment the fermentations are performed in the one or more fermentation containers. In an embodiment propagation of the alcohol producing microorganism and/or the organic acid producing microorganism by fermentation of the at least liquid fraction and/or the at least solid fraction is performed in one or more propagation containers. After propagation, the alcohol producing microorganism and/or the organic acid producing microorganism may be added to one or more fermentation containers. Alternatively, the propagation of the alcohol producing microorganism and/or the organic acid producing microorganism is combined with the fermentation of the at least liquid fraction and/or the at least solid fraction by the alcohol producing microorganism and/or the organic acid producing microorganism to produce alcohol and/or organic acid, respectively.

In an embodiment the alcohol producing microorganism is a microorganism that is able to ferment at least one C5 sugar. Preferably, it also is able to ferment at least one C6 sugar. In an embodiment the invention relates to an integrated process comprising the production of ethanol, wherein the process comprises the step of fermenting a medium containing sugar(s) with a microorganism that is able to ferment at least one C5 sugar.

In an embodiment the organic acid producing microorganism is a microorganism that is able to ferment at least one C6 sugar. In an embodiment the invention relates to an integrated process for the production of succinic acid, wherein the process comprises the step of fermenting a medium containing sugar(s) with a microorganism that is able to ferment at least one C6 sugar.

The alcohol producing microorganisms may be a prokaryotic or eukaryotic organism. The microorganism used in the process may be a genetically engineered microorganism. Examples of suitable alcohol producing organisms are yeasts, for instance *Saccharomyces*, e.g. *Saccharomyces cerevisiae, Saccharomyces pastorianus* or *Saccharomyces uvarum, Hansenula, Issatchenkia*, e.g. *Issatchenkia orientalis, Pichia*, e.g. *Pichia stipites* or *Pichia pastoris, Kluyveromyces*, e.g. *Kluyveromyces fagilis, Candida*, e.g. *Candida pseudotropicalis* or *Candida acidothermophilum, Pachysolen*, e.g. *Pachysolen tannophilus* or bacteria, for instance *Lactobacillus*, e.g. *Lactobacillus lactis, Geobacillus, Zymomonas*, e.g. *Zymomonas mobilis, Clostridium*, e.g. *Clostridium phytofermentans, Escherichia*, e.g. *E. coli, Klebsiella*, e.g. *Klebsiella oxytoca*. In an embodiment the microorganism that is able to ferment at least one C5 sugar is a yeast. In an embodiment, the yeast is belongs to the genus *Saccharomyces*, preferably of the species *Saccharomyces cerevisiae*. The yeast, e.g. *Saccharomyces cerevisiae*, used in the processes according to the present invention is capable of converting hexose (C6) sugars and pentose (C5) sugars. The yeast, e.g. *Saccharomyces cerevisiae*, used in the processes according to the present invention can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TAL1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

The volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g ethanol per g glucose or xylose.

In one aspect, the fermentation process leading to the production of ethanol, has several advantages by comparison to known ethanol fermentations processes: anaerobic processes are possible; oxygen limited conditions are possible; higher ethanol yields and ethanol production rates can be obtained; the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The organic acid producing microorganisms may be a prokaryotic or eukaryotic organism. The microorganism used in the process may be a genetically engineered microorganism. Examples of suitable organic acid producing organisms are yeasts, for instance *Saccharomyces*, e.g. *Saccharomyces cerevisiae*; fungi for instance *Aspergillus* strains, such as *Aspergillus niger* and *Aspergillus fumigatus*, *Byssochlamys nivea, Lentinus degener, Paecilomyces varioti* and *Penicillium viniferum*; and bacteria, for instance *Anaerobiospirillum succiniciproducens, Actinobacillus succinogenes, Mannhei succiniciproducers* MBEL 55E, *Escherichia coli, Propionibacterium* species, *Pectinatus* sp., *Bacteroides* sp., such as *Bacteroides amylophilus, Ruminococcus flavefaciens, Prevotella ruminicola, Succcinimonas amylolytica, Succinivibrio dextrinisolvens, Wolinella succinogenes*, and *Cytophaga succinicans*. In an embodiment the organic acid producing microorganism that is able to ferment at least one C6 sugar is a yeast. In an embodiment, the yeast is belongs to the genus *Saccharomyces*, preferably of the species *Saccharomyces cerevisiae*. The yeast, e.g. *Saccharomyces cerevisiae*, used in the production processes of organic acid according to the present invention is capable of converting hexose (C6) sugars. The yeast, e.g. *Saccharomyces cerevisiae*, used in the processes according to the present invention can anaerobically ferment at least one C6 sugar.

The fermentation processes may be carried out without any requirement to adjust the pH during the processes. That is to say, the processes are ones which may be carried out without the addition of any acid(s) or base(s). However, this excludes a pretreatment step, where acid may be added. The point is that the enzymes used in the processes of the invention is capable of acting at low pH and, therefore, there is no need to adjust the pH of acid of an acid pretreated feedstock in order that hydrolysis may take place. Accordingly, the processes of the invention may be zero waste processes using only organic products with no requirement for inorganic chemical input.

The overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly, lower overall reaction times may be reached at lower glucose yield.

Other fermentation products that may be produced by the integrated processes of the invention can be any substance derived from fermentation. They include, but are not limited to, alcohol (such as arabinitol, butanol, ethanol, glycerol, methanol, 1,3-propanediol, sorbitol, and xylitol); organic acid (such as acetic acid, acetonic acid, adipic acid, ascorbic acid, acrylic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, maleic acid, malic acid, malonic acid, oxalic acid, oxaloacetic acid, propionic acid, succinic acid, and xylonic acid); ketones (such as acetone); amino acids (such as aspartic acid, glutamic acid, glycine, lysine, serine, tryptophan, and threonine); alkanes (such as pentane, hexane, heptane, octane, nonane, decane, undecane, and dodecane), cycloalkanes (such as cyclopentane, cyclohexane, cycloheptane, and cyclooctane), alkenes (such as pentene, hexene, heptene, and octene); and gases (such as methane, hydrogen ($H_2$), carbon dioxide ($CO_2$), and carbon monoxide (CO)). The fermentation product can also be a protein, a vitamin, a pharmaceutical, an animal feed supplement, a specialty chemical, a chemical feedstock, a plastic, a solvent, ethylene, an enzyme, such as a protease, a cellulase, an amylase, a glucanase, a lactase, a lipase, a lyase, an oxidoreductase, a transferase or a xylanase. In a preferred embodiment the organic acid is succinic acid and/or the alcohol is ethanol.

In an embodiment the alcohol, the organic acid, the enzymes, the enzyme producing microorganism, the alcohol producing microorganism and/or the organic acid producing microorganism are recovered. The integrated processes according to the invention comprise recovery of all kinds of products made during the integrated processes including fermentation products such as ethanol and succinic acid. A fermentation product may be separated from the fermentation broth in manner know to the skilled person. Examples of techniques for recovery include, but are not limited to, chromatography, electrophoretic procedures, differential solubility, distillation, or extraction. For each fermentation product the skilled person will thus be able to select a proper separation technique. For instance, ethanol may be separated from a yeast fermentation broth by distillation, for instance steam distillation/vacuum distillation in conventional way.

In an embodiment the integrated processes of the invention also produce energy, heat, electricity and/or steam.

In an embodiment the solid fraction obtained after solid/liquid separation of the enzymatically hydrolysed lignocellulosic material, the waste obtained after purification/recovery of the organic acid, and/or the solids obtained after distillation/recovery of the ethanol can be used in the production of electricity. Electricity can be made by incineration of any one of the above-mentioned materials. The electricity can be used in any one of the steps of the integrated processes according to the present invention.

The beneficial effects of the present invention are found for several lignocellulosic materials and therefore believed to be present for the hydrolysis of all kind of lignocellulosic materials. This beneficial effects of the present invention are found for several enzymes and therefore believed to be present for all kind of hydrolysing enzyme compositions.

EXAMPLES

Example 1

Integrated Process for Alcohol Production and Organic Acid Production from Lignocellulosic Material A single batch of pretreated lignocellulosic material was separated by centrifugation into a solid fraction and liquid fraction. The solid fraction obtained after solid/liquid separation of the pretreated lignocellulosic material was washed to obtain a cellulose-rich pulp.

Part of the pulp was subjected to enzymatic hydrolysis. In this case, 64 kg dry matter pulp was hydrolysed in a 400 liter stirred vessel by adding it to 254 liter an aqueous composition containing cellulolytic enzymes from *Rasamsonia* (which was at a temperature of 62° C.). The first dosage of pulp resulted in 10% w/w dry matter of pH 4.2, which was liquefied by the enzymes within 3 hours. From that moment on, portions of 5 kg dry matter pulp were added each hour until 350 kg mash was obtained, while pH was adjusted to 4.2 with a 10% ammonia solution. The hydrolysis was continued while stirring at 62° C. for another 4 days and resulted in a glucose-rich hydrolysate.

The hydrolysate was centrifuged to obtain a solid fraction and a liquid fraction. The solid fraction was washed with water. The wash water was added to the liquid fraction and the combined liquid fractions were concentrated by evaporation until a final concentrated liquid fraction was obtained that contained glucose at a concentration of approximately 450 g/kg.

Part of the concentrated liquid fraction was used for propagation of genetically modified succinic acid overproducing yeast of the genus *Saccharomyces cerevisae*. The medium for propagation of the yeast was based on Verduyn glucose medium and contained ammonium sulphate, potassium phosphate, magnesium phosphate, trace elements and vitamins and 8 g/kg of the concentrated liquid fraction as carbon source (for Verduyn medium see Yeast 8, (1992), pages 201-517). Propagation was done for 68 hours in a stirred vessel at 30° C. with continuous stirring.

The so-obtained seed culture was added to inoculate a fermentor containing Verduyn medium with, among other components such as urea, biotin and calcium carbonate in defined concentrations. As carbon source, the concentrated liquid fraction was added by feeding it during the duration of the fermentation at a rate of 16 mL/kg·h. After 48 hours, the fermentation was stopped and the broth was centrifuged. The supernatant was subjected to repeatedly evaporation, crystallization, polishing and drying, resulting in crude succinic acid crystals.

Another part of the concentrated liquid fraction was used for propagation of an enzyme producing microorganism and production of enzymes by the enzyme producing microorganism. A fermentor containing mineral medium with 20 g/kg concentrate and 40 g/kg solid dry matter pulp was inoculated with the fungus *Rasamsonia emersonii*. During the first phase of the fermentation process, also called the growth phase or propagation phase, fungal biomass increases without protein production. In the second phase of the fermentation process, also called the enzyme production phase, enzymes are produced. The fermentation was performed under aseptic aerobic conditions at 37° C. pH 6 for 120 hours, while the concentrated liquid fraction was added as feed. The final protein concentration obtained at the end of fermentation was 65 g/kg supernatant. The obtained supernatant showed cellulolytic activity.

A part of the liquid fraction obtained after solid/liquid separation of the pretreated lignocellulosic material was mixed with a part of the concentrated liquid fraction to get a fermentable mixture. This mixture was fermented with the pentose fermenting *Saccharomyces cerevisae* strain RN1016 and yielded 5.1% w/w ethanol after fermentation for 48 hours at pH 5.5.

In a separate experiment, glucose-rich hydrolysate as such was fermented with *Saccharomyces cerevisae* strain RN1016 in a 34 hour fermentation at pH 4.2. The yield of ethanol on sugars was 90%.

Example 2

Integrated Process for Alcohol Production from Lignocellulosic Material

A single batch of pretreated lignocellulosic material was separated by centrifugation into a solid fraction and a liquid fraction. The liquid fraction was stored at 4° C. until use in the production of ethanol (see below). The solid fraction obtained after solid/liquid separation of the pretreated lignocellulosic material was washed to obtain a cellulose-rich pulp.

Part of the pulp was subjected to enzymatic hydrolysis. In this case, 64 kg dry matter pulp was hydrolysed in a 400 liter stirred vessel by adding it to 254 liter an aqueous composition containing cellulolytic enzymes from *Rasamsonia* (which was at a temperature of 62° C.). The first dosage of pulp resulted in 10% w/w dry matter of pH 4.2, which was liquefied by the enzymes within 3 hours. From that moment on, portions of 5 kg dry matter pulp were added each hour until 350 kg mash was obtained, while pH was adjusted to 4.2 with a 10% ammonia solution. The hydrolysis was continued while stirring at 62° C. for another 4 days and resulted in a glucose-rich hydrolysate.

The glucose-rich hydrolysate was centrifuged to obtain a solid fraction and a liquid fraction. The solid fraction was washed with water. The wash water was added to the liquid fraction and the combined liquid fractions were concentrated by evaporation until a final concentrated liquid fraction was obtained that contained glucose at a concentration of approximately 450 g/kg.

The liquid fraction obtained after pretreatment of the lignocellulosic material was divided into four equal portions. The first portion was kept as it is (undiluted portion) and fermented as such. The second portion was diluted to 70% w/w of its original concentration with water and fermented. The third portion was diluted to 70% w/w with 13% w/w concentrated liquid fraction and 17% w/w water and fermented. The fourth portion was diluted to 70% w/w with 20% w/w concentrated liquid fraction and 10% w/w water and fermented.

The portions were fermented with the pentose fermenting *Saccharomyces cerevisae* strain RN1016 for 48 hours at pH 5.5 to produce ethanol and the ethanol concentration was measured using HPLC. The measured ethanol concentration is expressed as % w/w fermented material at the end of the fermentation. The results are shown in Table 1.

Table 1 shows that diluting the liquid fraction obtained after pretreatment of the lignocellulosic material results in a higher ethanol yield. Table 1 also shows that even higher ethanol production yields were obtained when the liquid fraction obtained after pretreatment of the lignocellulosic material was diluted with a concentrated liquid fraction obtained after solid/liquid separation of the hydrolysate compared to when the liquid fraction obtained after pretreatment of the lignocellulosic material was diluted with water only.

Example 3

Integrated Process for Alcohol Production from Lignocellulosic Material

The example is done essentially as described in Example 2 with the proviso that the dilution is not done with the concentrated liquid fraction, but with the solid fraction obtained after solid/liquid separation of the hydrolysate. The solid fraction contains residual soluble sugars (about 17% w/w of total solids in the solid fraction) that are entrapped in the remaining insoluble sugar fraction and lignin present in the solid fraction.

The liquid fraction is diluted to 70% w/w/with the solid fraction. Dilution with the solid fraction results in a higher ethanol concentration (about 4% w/w ethanol).

Example 4

Integrated Process for Production of Enzymes by an Enzyme Producing Microorganism A single batch of pretreated lignocellulosic material was separated by centrifugation into a solid fraction and a liquid fraction. The solid fraction obtained after solid/liquid separation of the pretreated lignocellulosic material was washed to obtain cellulose-rich solids.

Part of the solids was used as a substrate (called substrate A) to induce enzyme production. Another part of the solids was subjected to enzymatic hydrolysis as described in Example 1. The hydrolysate obtained after enzymatic hydrolysis was centrifuged to obtain a solid fraction and a liquid fraction. The solid fraction (called substrate B) was washed with water and used to induce enzyme production.

The wash water was added to the liquid fraction and the resulting liquid fraction was concentrated by evaporation until a final concentrated liquid fraction was obtained that contained glucose at a concentration of approximately 450 g/kg.

The concentrated liquid fraction was used as a carbon source in two enzyme production processes in the fungus *Rasamsonia*. In one process, substrate A was used as enzyme production inducer, while in the other process, substrate B was used as an enzyme production inducer. The production processes consisted of a growth phase and an enzyme production phase. At the end of the enzyme production phase, the amount of enzyme present in the liquid fraction of the fermentation broth was determined using a standard protein determination assay and showed to be of a comparable level (50+/−5 g/L), demonstrating that both the solid fraction obtained after solid/liquid separation of pretreated lignocellulosic material as such and the solid fraction obtained after solid/liquid separation of an enzymatic hydrolysate can be used as inducer in enzyme production.

TABLE 1

Ethanol production after a fermentation of 48 hours of diluted and undiluted portions.

| | Ethanol concentration (in % w/w) |
|---|---|
| Portion 1 (undiluted) | 1.2 |
| Portion 2 (diluted to 70% with water) | 2.0 |
| Portion 3 (diluted to 70% with 13% concentrated liquid fraction and 17% water) | 4.5 |
| Portion 4 (diluted to 70% with 20% concentrated liquid fraction and 10% water) | 5.3 |

The invention claimed is:

1. An integrated process for alcohol production from lignocellulosic material, wherein the process comprises:
   pretreatment of the lignocellulosic material to obtain pretreated lignocellulosic material;
   enzymatic hydrolysis of a part of the pretreated lignocellulosic material to obtain enzymatically hydrolysed lignocellulosic material;
   propagation of an alcohol producing microorganism by fermentation of a part of the pretreated lignocellulosic material and fermentation of the enzymatically hydrolysed lignocellulosic material by the alcohol producing microorganism to produce alcohol, wherein the alcohol producing microorganism is able to ferment at least a C5 sugar and at least a C6 sugar;
   propagation of a fungus and production of enzymes by the fungus, wherein a part of the pretreated lignocellulosic material is used in the propagation of the fungus and/or the production of enzymes by the fungus, and wherein the enzymes produced by the fungus are used in the enzymatic hydrolysis.

2. The process according to claim 1, wherein a part of the enzymatically hydrolysed lignocellulosic material and a part of the lignocellulosic material are used in the propagation of the enzyme producing microorganism and/or the production of enzymes by the enzyme producing microorganism.

3. The process according to claim 1, wherein the enzymatic hydrolysis comprises at least:
   a liquefaction step wherein the lignocellulosic material is hydrolysed in at least a first container, and
   a saccharification step wherein the liquefied lignocellulosic material is hydrolysed in the at least first container and/or in at least a second container.

4. The process according to claim 1, wherein the alcohol, the enzymes, the enzyme producing microorganism and/or the alcohol producing microorganism are recovered.

5. The process according to claim 1, wherein oxygen is added during the enzymatic hydrolysis.

6. The process according to claim 1, wherein the fungus is *Rasamsonia*.

7. The process according to claim 1, wherein the enzymes are comprised in a whole fermentation broth.

8. The process according to claim 1, wherein the alcohol producing microorganism is a yeast.

9. The process according to claim 1, wherein the alcohol producing microorganism is *Saccharomyces cerevisiae*.

10. The process according to claim 1, wherein the dry matter content at the end of the enzymatic hydrolysis is 5 wt % or higher.

11. The process according to claim 1, wherein the alcohol is ethanol.

12. The process according to claim 1, wherein the enzymatic hydrolysis and fermentation are separate steps.

13. The process according to claim 1, wherein the enzymatic hydrolysis and fermentation are combined.

* * * * *